(12) United States Patent
Blacker et al.

(10) Patent No.: US 7,905,228 B2
(45) Date of Patent: Mar. 15, 2011

(54) NEBULIZER APPARATUS AND METHOD

(75) Inventors: Rick Blacker, London (CA); Evan Goodwin, Bowmanville (CA)

(73) Assignee: Trudell Medical International, London, Ontario (CA)

( * ) Notice: Subject to any disclaimer, the term of this patent is extended or adjusted under 35 U.S.C. 154(b) by 822 days.

(21) Appl. No.: 11/542,619

(22) Filed: Oct. 3, 2006

(65) Prior Publication Data

US 2007/0107719 A1    May 17, 2007

Related U.S. Application Data

(63) Continuation of application No. 11/046,217, filed on Jan. 27, 2005, now Pat. No. 7,131,439, which is a continuation of application No. 10/101,554, filed on Mar. 19, 2002, now Pat. No. 6,929,003.

(60) Provisional application No. 60/277,482, filed on Mar. 20, 2001.

(51) Int. Cl.
*A61M 11/00* (2006.01)
*B05B 1/26* (2006.01)

(52) U.S. Cl. ......... 128/200.14; 128/200.18; 128/200.11; 128/200.22; 128/203.12; 222/3; 222/4; 222/402.17

(58) Field of Classification Search ............. 128/200.11, 128/200.22, 200.24, 203.12–203.18, 203.25–203.27, 128/205.23; 222/3, 4, 402.17; 239/338, 239/370
See application file for complete search history.

(56) References Cited

U.S. PATENT DOCUMENTS

| | | | |
|---|---|---|---|
| 2,535,844 A | 12/1950 | Emerson | |
| 2,882,026 A | 4/1959 | Eichelman | |
| 2,951,644 A | 9/1960 | Mahon et al. | |
| 3,172,406 A | 3/1965 | Bird et al. | |
| 3,269,665 A | 8/1966 | Cheney | |
| 3,467,092 A | 9/1969 | Bird et al. | |
| 3,490,697 A | 1/1970 | Best, Jr. | |
| 3,580,249 A | 5/1971 | Takaoka | |
| 3,584,621 A | 6/1971 | Bird et al. | |
| 3,630,196 A | 12/1971 | Bird et al. | |
| 3,658,059 A | 4/1972 | Steil | |
| 3,664,337 A | 5/1972 | Lindsey et al. | |

(Continued)

FOREIGN PATENT DOCUMENTS

AU     B-29969/89     8/1990

(Continued)

OTHER PUBLICATIONS

Claims for pending U.S. Appl. No. 09/447,016, filed Nov. 22, 1999, entitled "Breath Actuated Nebulizer With Valve Assembly Having A Relief Piston".

(Continued)

*Primary Examiner* — Steven O Douglas
*Assistant Examiner* — Valerie Skorupa
(74) *Attorney, Agent, or Firm* — Brinks Hofer Gilson & Lione

(57) ABSTRACT

A nebulizer for efficiently and reliably delivering aerosolized fluid to an inhaling patient is disclosed. The nebulizer includes a fixed diverter and a movable fluid orifice or fluid pathway connected with an actuator for responding to an inhalation or a manual actuation and beginning the nebulization process. Also provided is a method of providing nebulization including the steps of moving a fluid orifice or fluid pathway connected to an actuator so that the fluid orifice or fluid pathway reaches a nebulizing position during inhalation.

16 Claims, 14 Drawing Sheets

U.S. PATENT DOCUMENTS

| | | |
|---|---|---|
| 3,826,255 A | 7/1974 | Havstad et al. |
| 3,838,686 A | 10/1974 | Szekely |
| 3,874,379 A | 4/1975 | Enfield et al. |
| 3,903,884 A | 9/1975 | Huston et al. |
| 3,990,442 A | 11/1976 | Patneau |
| 4,093,124 A | 6/1978 | Morane et al. |
| 4,094,317 A | 6/1978 | Wasnich |
| 4,106,503 A | 8/1978 | Rosenthal et al. |
| 4,116,387 A * | 9/1978 | Kremer et al. ............... 239/338 |
| 4,139,128 A * | 2/1979 | Ewald ..................... 222/402.17 |
| 4,150,071 A | 4/1979 | Pecina |
| 4,183,361 A | 1/1980 | Russo |
| 4,198,969 A | 4/1980 | Virag |
| 4,206,644 A | 6/1980 | Platt |
| 4,210,140 A | 7/1980 | James et al. |
| 4,210,155 A | 7/1980 | Grimes |
| 4,251,033 A | 2/1981 | Rich et al. |
| 4,253,468 A | 3/1981 | Lehmbeck |
| 4,268,460 A | 5/1981 | Boiarski et al. |
| 4,291,688 A | 9/1981 | Kistler |
| 4,333,450 A | 6/1982 | Lester |
| 4,413,784 A | 11/1983 | Dea |
| 4,456,179 A * | 6/1984 | Kremer ........................ 239/338 |
| 4,470,412 A | 9/1984 | Nowacki et al. |
| 4,484,577 A | 11/1984 | Sackner et al. |
| 4,508,118 A | 4/1985 | Toth |
| 4,509,668 A | 4/1985 | Klaus et al. |
| 4,588,129 A | 5/1986 | Shanks |
| 4,620,670 A | 11/1986 | Hughes |
| 4,627,432 A | 12/1986 | Newell et al. |
| 4,657,007 A | 4/1987 | Carlin et al. |
| 4,674,491 A | 6/1987 | Brugger et al. |
| 4,677,975 A | 7/1987 | Edgar et al. |
| 4,746,067 A | 5/1988 | Svoboda |
| 4,758,224 A | 7/1988 | Siposs |
| 4,792,097 A | 12/1988 | Kremer, Jr. et al. |
| 4,809,692 A | 3/1989 | Nowacki et al. |
| 4,832,015 A | 5/1989 | Nowacki et al. |
| 4,911,157 A | 3/1990 | Miller |
| 4,984,158 A | 1/1991 | Hillsman |
| 5,012,803 A | 5/1991 | Foley et al. |
| 5,012,804 A | 5/1991 | Foley et al. |
| 5,020,527 A | 6/1991 | Dessertine |
| 5,020,530 A | 6/1991 | Miller |
| 5,042,467 A | 8/1991 | Foley |
| 5,054,477 A | 10/1991 | Terada et al. |
| 5,054,478 A | 10/1991 | Grychowski et al. |
| 5,078,131 A | 1/1992 | Foley |
| 5,086,765 A | 2/1992 | Levine |
| 5,165,392 A | 11/1992 | Small |
| 5,167,506 A | 12/1992 | Kilis et al. |
| 5,170,782 A | 12/1992 | Kocinski |
| 5,241,954 A | 9/1993 | Glenn |
| 5,277,175 A | 1/1994 | Riggs et al. |
| 5,280,784 A | 1/1994 | Kohler |
| 5,299,565 A | 4/1994 | Brown |
| 5,301,662 A | 4/1994 | Bagwell et al. |
| 5,301,663 A | 4/1994 | Small, Jr. |
| 5,309,900 A | 5/1994 | Knoch et al. |
| 5,312,046 A | 5/1994 | Knoch et al. |
| 5,312,281 A | 5/1994 | Takahashi et al. |
| 5,318,015 A | 6/1994 | Mansson et al. |
| 5,333,106 A | 7/1994 | Lanpher et al. |
| 5,337,926 A * | 8/1994 | Drobish et al. ............... 222/309 |
| 5,349,947 A | 9/1994 | Newhouse et al. |
| 5,363,842 A | 11/1994 | Mishelevich et al. |
| 5,383,470 A | 1/1995 | Kolbly |
| 5,385,140 A | 1/1995 | Smith |
| 5,392,648 A | 2/1995 | Robertson |
| 5,398,714 A | 3/1995 | Price |
| 5,427,089 A | 6/1995 | Kraemer |
| 5,431,154 A | 7/1995 | Seigel et al. |
| 5,458,136 A | 10/1995 | Jaser et al. |
| 5,461,695 A | 10/1995 | Knoch |
| 5,479,920 A | 1/1996 | Piper et al. |
| 5,487,378 A | 1/1996 | Robertson et al. |
| 5,497,765 A | 3/1996 | Praud et al. |
| 5,505,192 A | 4/1996 | Samiotes et al. |
| 5,505,193 A | 4/1996 | Baliini et al. |
| 5,511,538 A | 4/1996 | Haber et al. |
| 5,511,539 A | 4/1996 | Lien |
| 5,515,842 A | 5/1996 | Ramseyer et al. |
| 5,520,166 A | 5/1996 | Ritson et al. |
| 5,522,380 A | 6/1996 | Dwork |
| 5,533,497 A | 7/1996 | Ryder |
| 5,533,501 A | 7/1996 | Denyer |
| 5,544,647 A | 8/1996 | Jewett et al. |
| 5,549,102 A | 8/1996 | Lintl et al. |
| 5,570,682 A | 11/1996 | Johnson |
| 5,582,162 A | 12/1996 | Petersson |
| 5,584,285 A | 12/1996 | Salter et al. |
| 5,598,839 A | 2/1997 | Niles et al. |
| 5,613,489 A | 3/1997 | Miller et al. |
| 5,617,844 A | 4/1997 | King |
| 5,622,162 A | 4/1997 | Johansson et al. |
| 5,630,409 A | 5/1997 | Bono et al. |
| 5,645,049 A | 7/1997 | Foley et al. |
| 5,687,912 A | 11/1997 | Denyer |
| 5,701,886 A | 12/1997 | Ryatt |
| 5,704,344 A | 1/1998 | Cole |
| 5,740,793 A | 4/1998 | Hodson et al. |
| 5,752,505 A | 5/1998 | Ohki et al. |
| 5,758,638 A | 6/1998 | Kreamer |
| 5,765,553 A | 6/1998 | Richards et al. |
| 5,792,057 A | 8/1998 | Rubsamen et al. |
| 5,803,078 A | 9/1998 | Brauner |
| 5,816,240 A | 10/1998 | Komesaroff |
| 5,823,179 A | 10/1998 | Grychowski et al. |
| 5,848,588 A | 12/1998 | Foley et al. |
| 5,865,172 A | 2/1999 | Butler et al. |
| 5,875,774 A | 3/1999 | Clementi et al. |
| 5,881,718 A | 3/1999 | Mortensen et al. |
| 5,899,201 A | 5/1999 | Schultz et al. |
| 5,937,852 A | 8/1999 | Butler et al. |
| 5,954,049 A | 9/1999 | Foley et al. |
| 5,988,160 A | 11/1999 | Foley et al. |
| 6,026,807 A | 2/2000 | Puderbaugh et al. |
| 6,033,841 A | 3/2000 | Bell et al. |
| 6,039,042 A | 3/2000 | Sladek |
| 6,044,841 A | 4/2000 | Verdun et al. |
| 6,073,628 A | 6/2000 | Butler et al. |
| 6,116,233 A | 9/2000 | Denyer et al. |
| 6,116,239 A | 9/2000 | Volgyesi |
| 6,129,080 A | 10/2000 | Pitcher et al. |
| 6,131,568 A | 10/2000 | Denyer et al. |
| 6,176,237 B1 | 1/2001 | Wunderlich et al. |
| 6,179,164 B1 | 1/2001 | Fuchs |
| 6,223,745 B1 | 5/2001 | Hammerlund et al. |
| 6,237,589 B1 | 5/2001 | Denyer et al. |
| 6,253,767 B1 | 7/2001 | Mantz |
| 6,293,279 B1 | 9/2001 | Schmidt et al. |
| 6,338,443 B1 * | 1/2002 | Piper ........................... 239/340 |
| 6,345,617 B1 | 2/2002 | Engelbreth et al. |
| 6,435,177 B1 | 8/2002 | Schmidt et al. |
| 6,450,163 B1 | 9/2002 | Blacker et al. |
| 6,513,519 B2 | 2/2003 | Gallem |
| 6,543,448 B1 | 4/2003 | Smith et al. |
| 6,557,549 B2 | 5/2003 | Schmidt et al. |
| 6,578,571 B1 | 6/2003 | Watt |
| 6,584,971 B1 | 7/2003 | Denyer et al. |
| 6,595,203 B1 | 7/2003 | Bird |
| 6,606,992 B1 | 8/2003 | Schuler et al. |
| 6,612,303 B1 | 9/2003 | Grychowski et al. |
| 6,644,304 B2 | 11/2003 | Grychowski et al. |
| 6,679,250 B2 | 1/2004 | Walker et al. |
| 6,708,688 B1 | 3/2004 | Rubin et al. |
| 6,748,945 B2 | 6/2004 | Grychowski et al. |
| 6,823,862 B2 | 11/2004 | McNaughton |
| 6,848,443 B2 | 2/2005 | Schmidt et al. |
| 6,857,427 B2 | 2/2005 | Ziegler et al. |
| 6,904,908 B2 | 6/2005 | Bruce et al. |
| 6,929,003 B2 | 8/2005 | Blacker et al. |
| 6,994,083 B2 | 2/2006 | Foley et al. |
| 7,013,896 B2 | 3/2006 | Schmidt |
| 7,036,505 B2 | 5/2006 | Bacon et al. |
| 7,051,731 B1 | 5/2006 | Rogerson |
| 7,080,643 B2 | 7/2006 | Grychowski et al. |

| | | |
|---|---|---|
| 7,131,439 B2 | 11/2006 | Blacker et al. |
| 7,131,440 B2 | 11/2006 | Sonntag |
| 7,201,165 B2 | 4/2007 | Bruce et al. |
| 7,261,102 B2 | 8/2007 | Barney et al. |
| 7,270,123 B2 | 9/2007 | Grychowski et al. |
| 7,559,322 B2 | 7/2009 | Foley et al. |
| 7,568,480 B2 | 8/2009 | Foley et al. |
| 7,634,995 B2 | 12/2009 | Grychowski et al. |
| 2001/0032643 A1 | 10/2001 | Hochrainer et al. |
| 2002/0020762 A1 | 2/2002 | Selzer et al. |
| 2002/0104531 A1 | 8/2002 | Malone |
| 2002/0157663 A1 | 10/2002 | Blacker |
| 2003/0005929 A1 | 1/2003 | Grychowski et al. |
| 2003/0015193 A1 | 1/2003 | Grychowski et al. |
| 2003/0136399 A1 | 7/2003 | Foley et al. |
| 2003/0159694 A1 | 8/2003 | McNaughton |
| 2004/0031485 A1 | 2/2004 | Rustad et al. |
| 2004/0060556 A1 | 4/2004 | Halamish |
| 2004/0173209 A1 | 9/2004 | Grychowski et al. |
| 2004/0231665 A1 | 11/2004 | Lieberman et al. |
| 2005/0039741 A1 | 2/2005 | Gallem et al. |
| 2005/0183718 A1 | 8/2005 | Wuttke et al. |
| 2006/0011196 A2 | 1/2006 | Gallem et al. |
| 2007/0204864 A1 | 9/2007 | Grychowski et al. |
| 2008/0083407 A1 | 4/2008 | Grychowski et al. |
| 2008/0257345 A1 | 10/2008 | Snyder et al. |
| 2009/0272820 A1 | 11/2009 | Foley et al. |

FOREIGN PATENT DOCUMENTS

| | | |
|---|---|---|
| DE | 8703534 U1 | 8/1987 |
| DE | 199 02 847 C1 | 5/2000 |
| DE | 199 53 317 C1 | 2/2001 |
| EP | 0 281 650 A1 | 9/1988 |
| EP | 0 281 650 B1 | 9/1988 |
| EP | 0 414 536 A2 | 2/1991 |
| EP | 0 514 085 A1 | 11/1992 |
| EP | 0 587 380 B1 | 3/1993 |
| EP | 0587380 | 3/1994 |
| EP | 0 601 708 A2 | 6/1994 |
| EP | 0 641 570 A1 | 3/1995 |
| EP | 0 711 609 A3 | 10/1996 |
| EP | 0 855 224 A2 | 7/1998 |
| EP | 0 938 906 A2 | 9/1999 |
| EP | 0 601 708 B1 | 3/2000 |
| FR | 1 070 292 | 7/1954 |
| FR | 2 763 507 A1 | 11/1998 |
| GB | 497530 | 12/1938 |
| GB | 675524 | 7/1952 |
| GB | 1 598 081 | 9/1981 |
| GB | 2 253 200 A | 9/1992 |
| GB | 2 299 512 A | 10/1996 |
| GB | 2 310 607 A | 9/1997 |
| WO | 90/09203 | 8/1990 |
| WO | 94/17753 A1 | 8/1994 |
| WO | 98/26828 | 6/1998 |
| WO | 98/41265 | 9/1998 |
| WO | 98/44974 | 10/1998 |
| WO | 99/40959 | 8/1999 |
| WO | 99/53982 | 10/1999 |
| WO | 00/59565 | 10/2000 |
| WO | 02/24263 A2 | 3/2002 |

OTHER PUBLICATIONS

Claims for pending U.S. Appl. No. 09/168,132, filed Oct. 7, 1998, entitled "Nebulizer Apparatus And Method".

International Search Report issued in international application No. PCT/IB02/00744, dated Nov. 11, 2002, 4 pages.

PARI LC Plus Instructions for Use (GB), PARI GmbH, dated Jul. 2001, 19 pages.

Photographs of nebulizer manufactured by PARI GmbH with detachable gas flow interrupter believed to have been publicly available prior to Feb. 13, 1996, 7 pages.

Product information excerpt, Boehringer Ingelheim, from website http://www.torpex.com/product_information/, Aug. 11, 2003, 4 pages.

Product Information, Boerhinger Ingelheim, "Introducing TORPEX ™ (aerosol albuterol sulfate): The Ultimate Tool for Equine Inhalation Treatment", from website http://www.tomex.eorn/product_information/, Mar. 21, 2002, 3 pages.

* cited by examiner

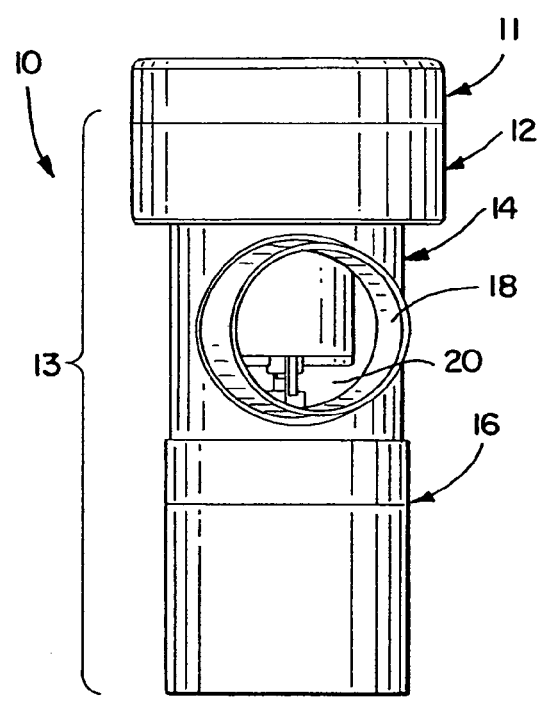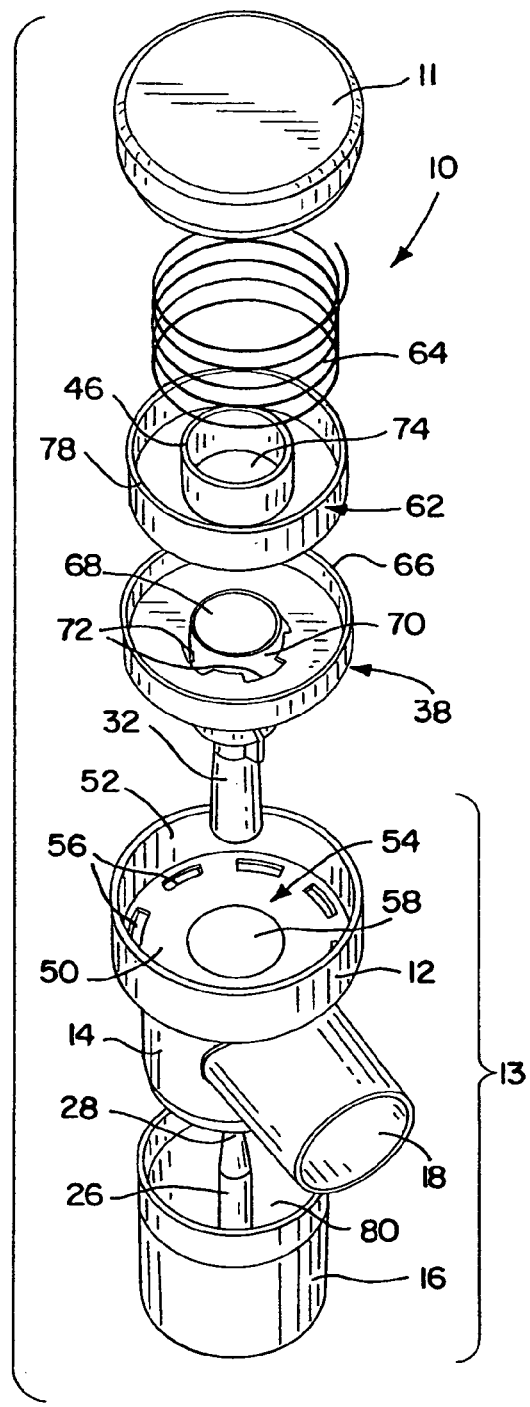

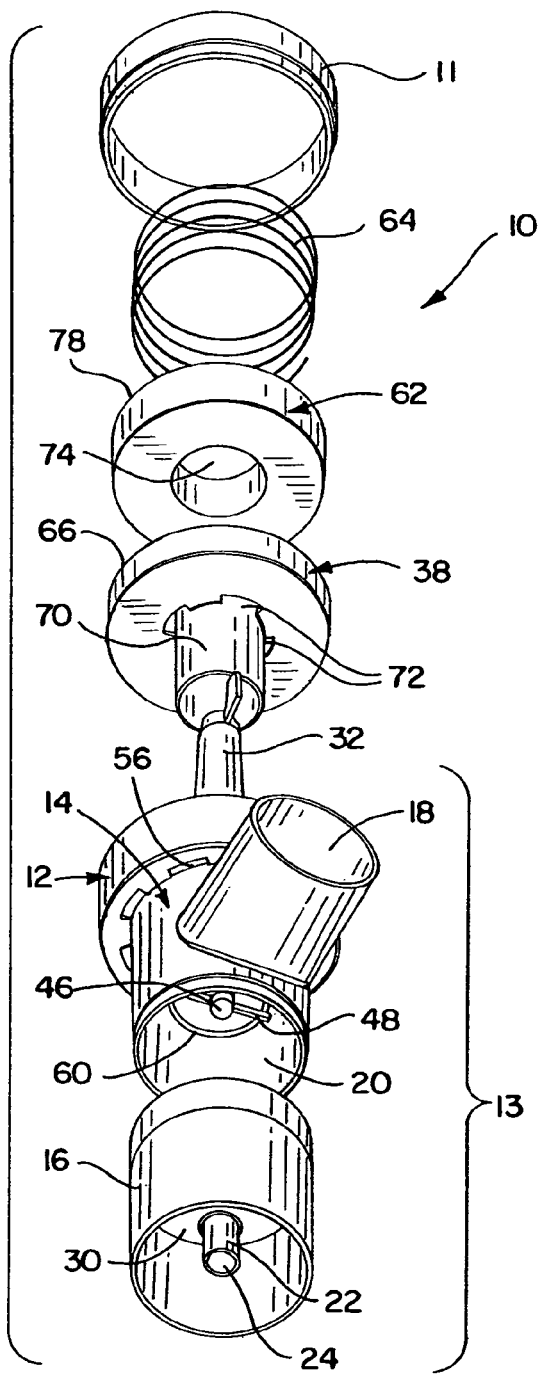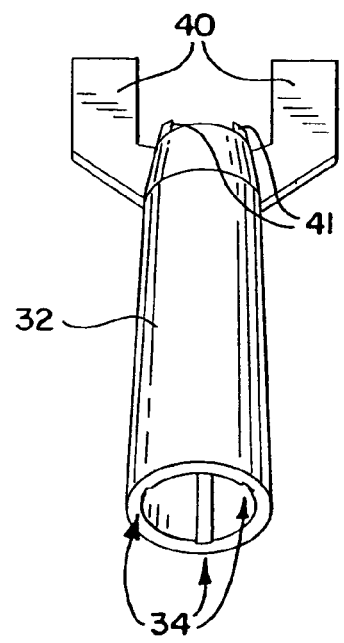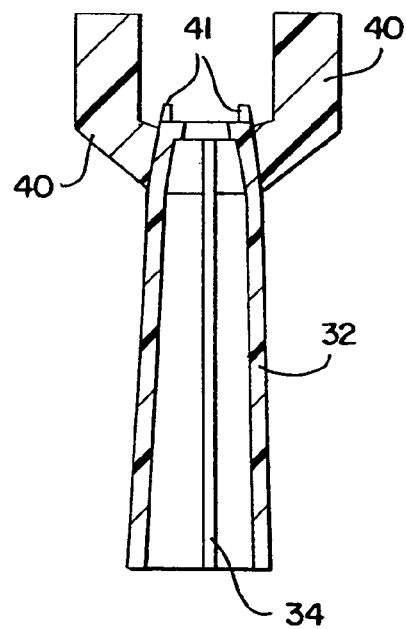

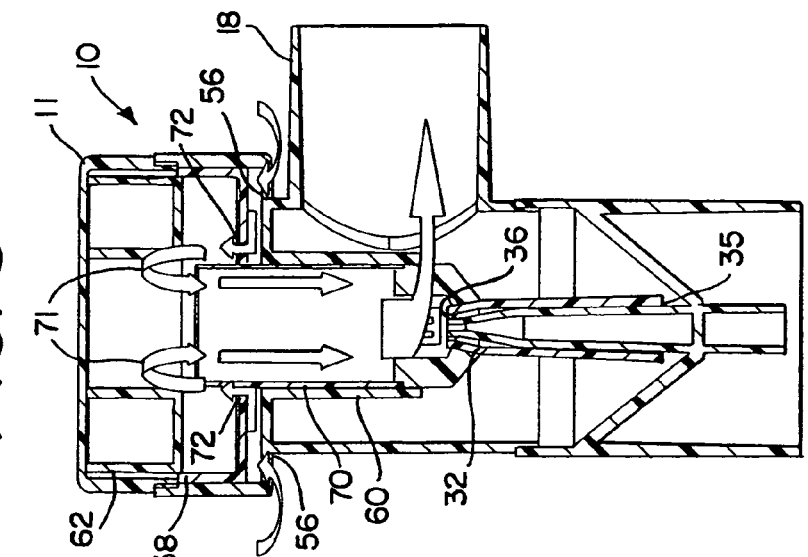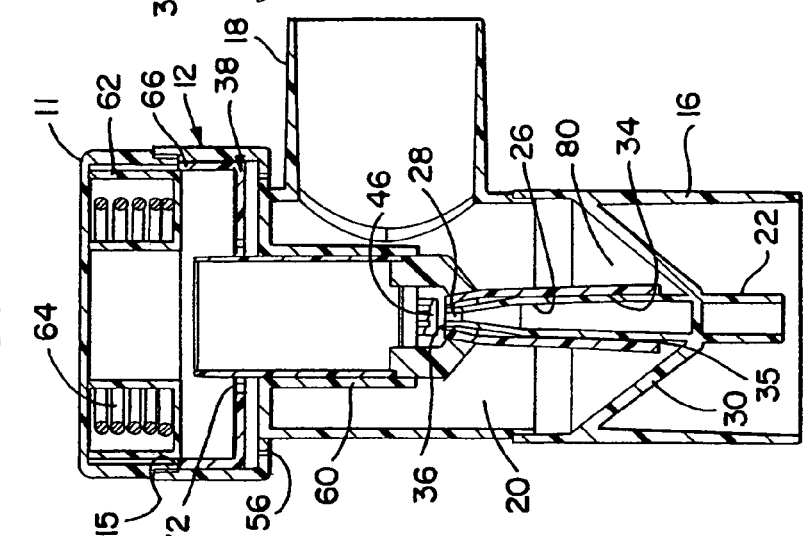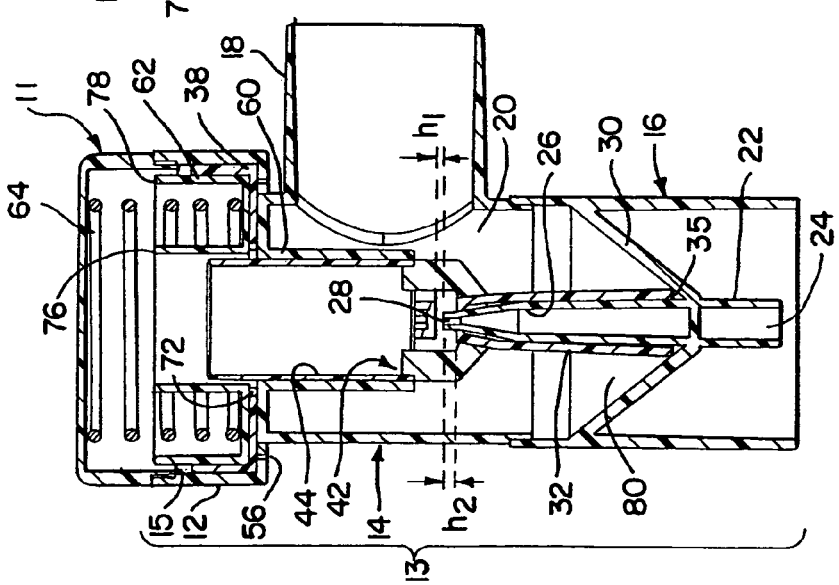

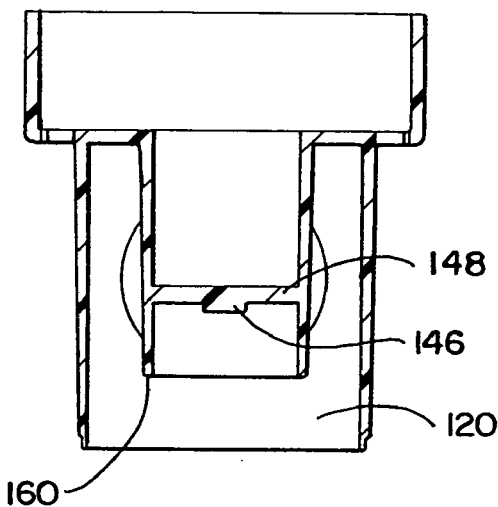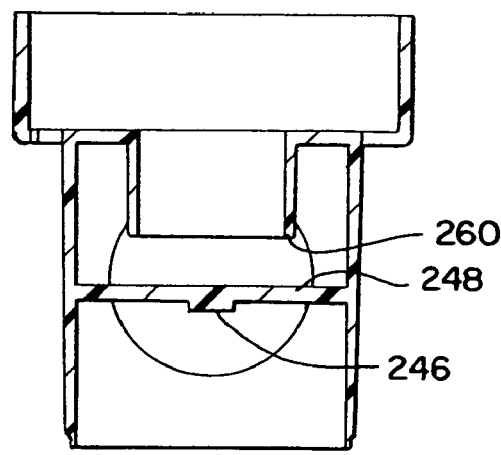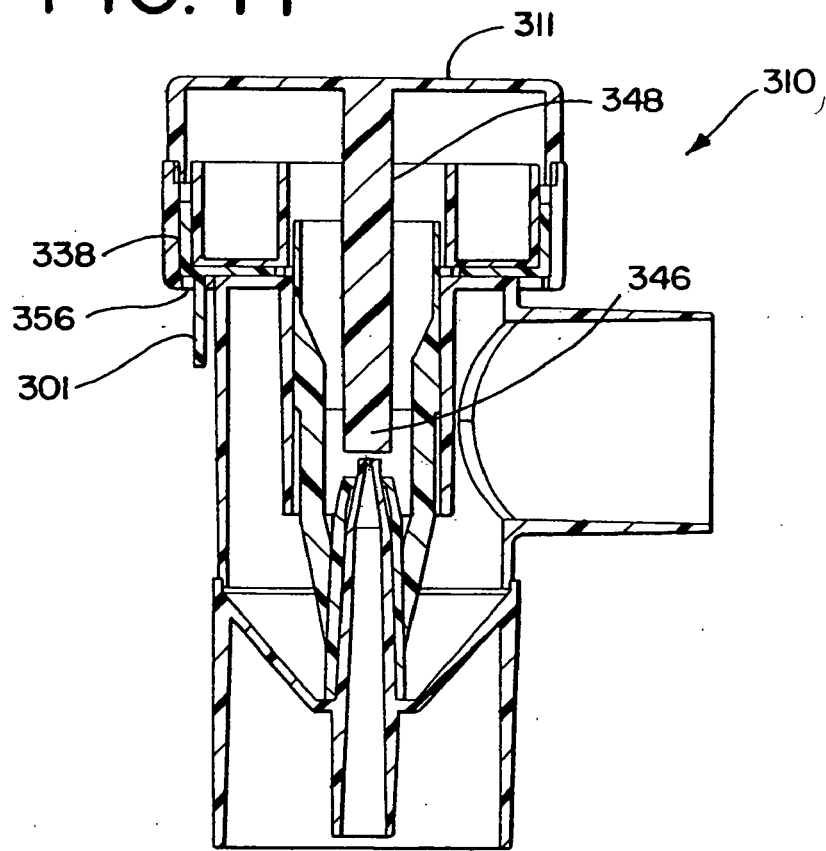

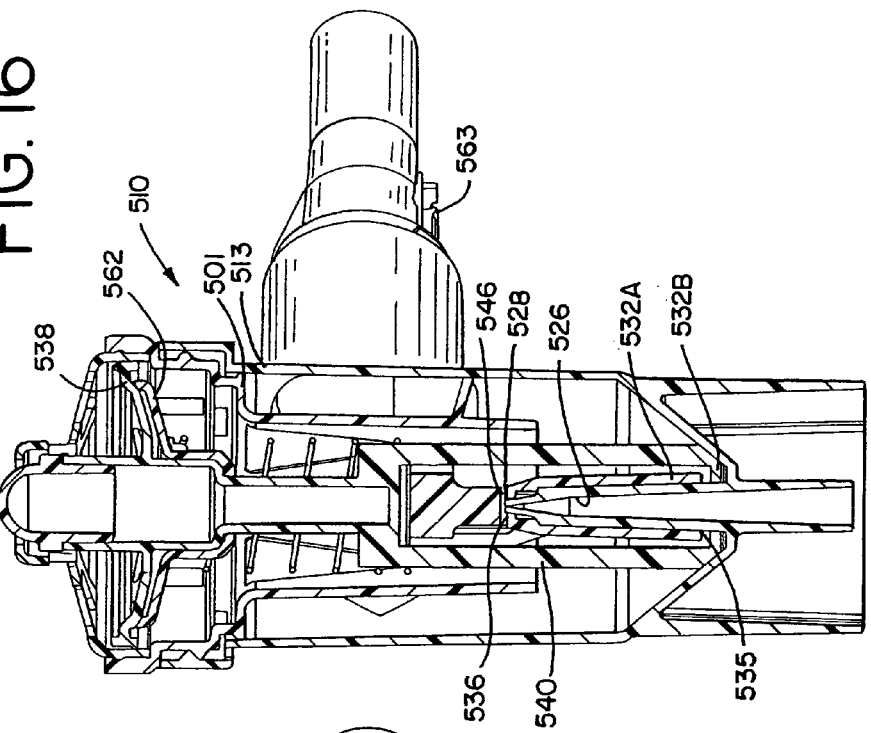
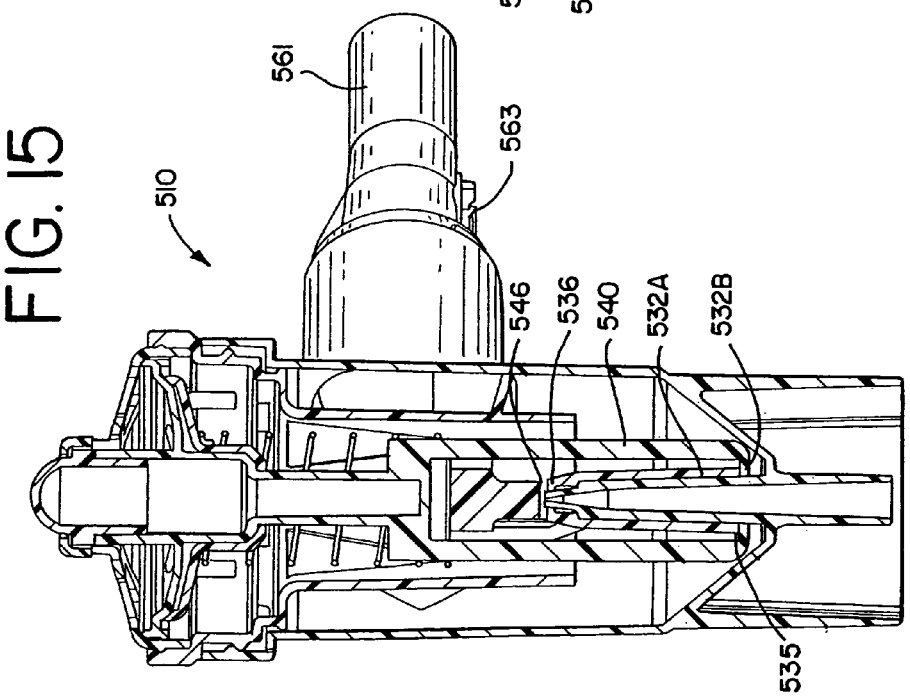

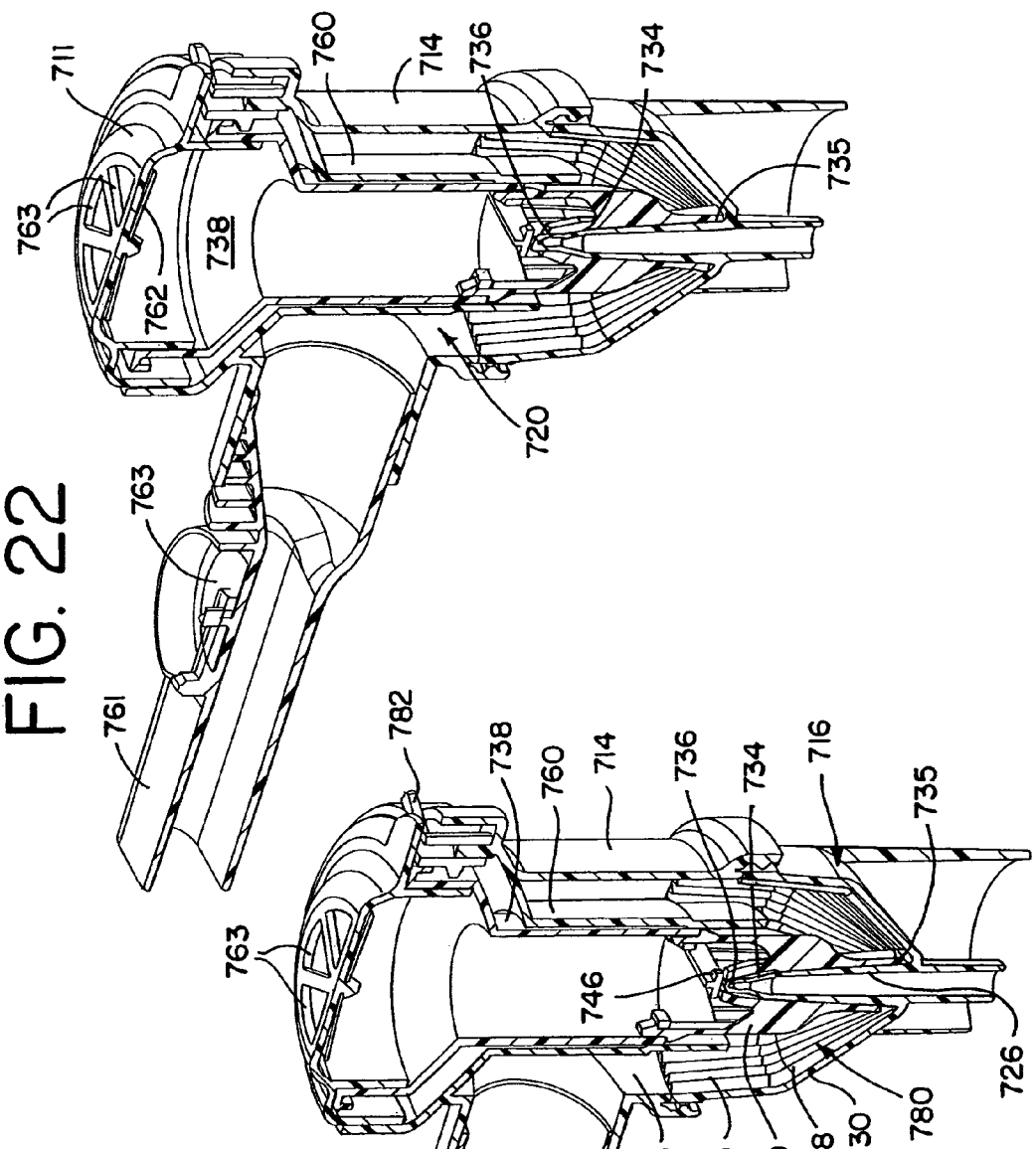
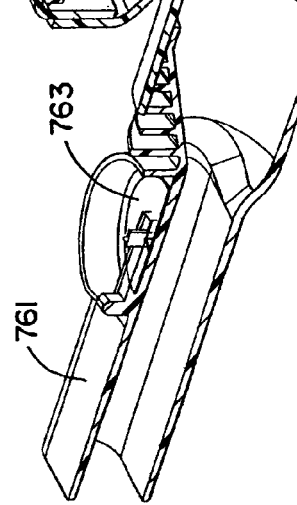
FIG. 22
FIG. 23

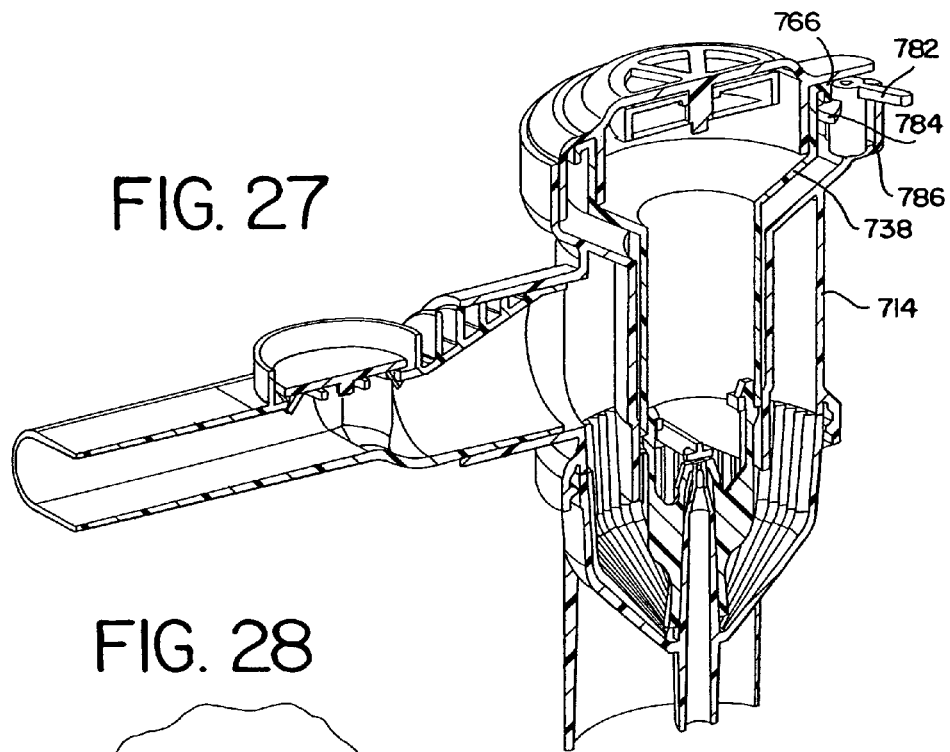
FIG. 27
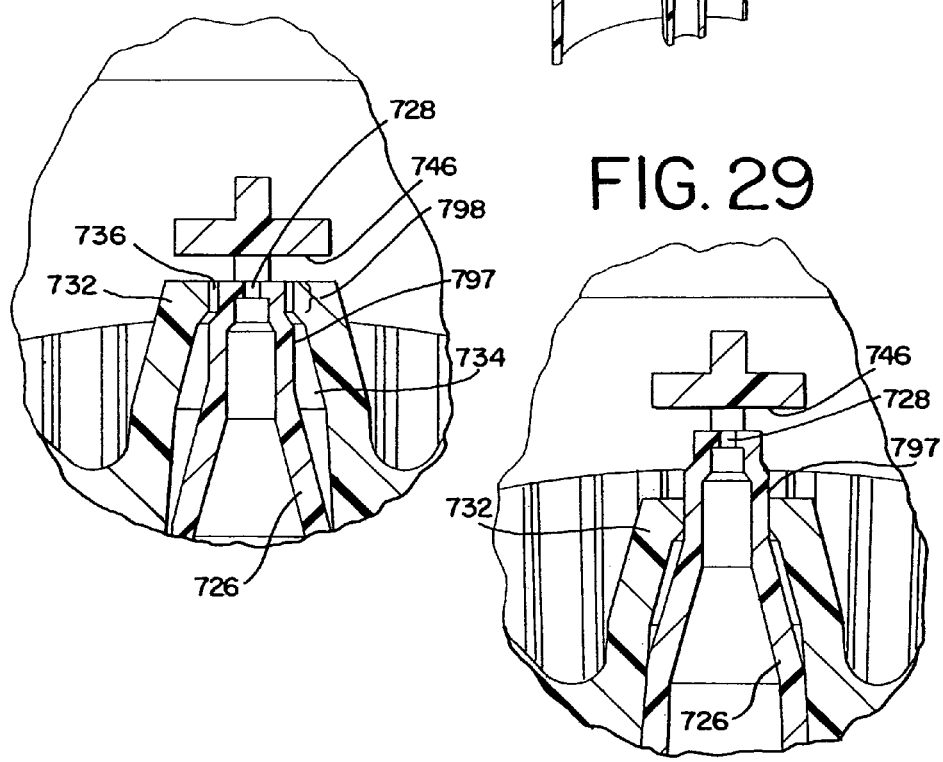
FIG. 28
FIG. 29

NEBULIZER APPARATUS AND METHOD

CROSS-REFERENCE TO RELATED APPLICATIONS

This application is a continuation of U.S. application Ser. No. 11/046,217, filed Jan. 27, 2005, now U.S. Pat. No. 7,131,439 which is a continuation of U.S. application Ser. No. 10/101,554, filed Mar. 19, 2002, now U.S. Pat. No. 6,929,003, which claims the benefit of provisional application Ser. No. 60/277,482, filed Mar. 20, 2001, wherein the entire disclosure of each of these applications is incorporated herein by reference.

FIELD OF THE INVENTION

The present invention relates to a method and apparatus for generating an aerosol for delivery to a patient. More particularly, the present invention relates to a nebulizer configured to nebulize a fluid into an aerosol in coordination with a patient's breathing.

BACKGROUND

Medical nebulizers that nebulize a fluid into an aerosol for inhalation by a patient are well-known devices commonly used for the treatment of certain conditions and diseases. Nebulizers have applications for conscious, spontaneously-breathing patients and for controlled, ventilated patients.

In some nebulizers, a gas and a fluid are mixed together and directed against a baffle or diverter. In some other nebulizers, interaction of the gas and fluid is enhanced through impacting the gas and fluid against a diverter. The term diverter, as used in this specification, includes any baffle or impinger. As a result of either nebulization process described above, the fluid is transformed into an aerosol, that is, the fluid is caused to form small particles that are suspended in the air and that have a particle size in a range suitable for delivery to a targeted area of a patient's respiratory tract. One way to mix the gas and fluid together in a nebulizer is to pass a quickly moving gas over a fluid orifice tip of a tube. The negative pressure created by the flow of pressurized gas is a factor that contributes to drawing fluid out of the fluid orifice into the stream of gas and nebulizing it.

Important considerations in the design of a nebulizer are the timing and dosage regulation of the aerosolized fluid. In some nebulizer designs, a continuous stream of pressurized gas entrains the fluid against the diverter to constantly generate an aerosol until the fluid in a reservoir is depleted. Continuous nebulization may result in a waste of aerosol during a patient's exhalation or during a delay between inhalation and exhalation. The amount of wasted aerosol may be difficult to quantify and some of the aerosol may be lost to condensation on the nebulizer or mouthpiece during periods of non-inhalation. Nebulizers implementing a timed or non-continuous nebulization may adversely affect particle size and density as the nebulization is turned on and off.

Effective and economical nebulizer therapy includes the ability to quickly generate a large amount of aerosol within a predetermined particle size range. An effective nebulizer preferably provides these features synchronously with the inhalation of the patient. In order to actuate a mechanical nebulizer, a patient's inhalation effort must overcome certain variables. Depending on the structural configuration of the nebulizer, these variables may include one or more of the following: the volumetric flow rate of the flowing gas; air leaks in the device; the force exerted by the flowing gas on a moveable diverter; and the friction between moveable parts. The greater the flow rate, air leaks and friction, the greater the inhalation effort required in order to actuate the device. It is desirable that a nebulizer have adequate sensitivity to quickly respond to an inhalation while not adversely restricting the patient's inhalation.

BRIEF SUMMARY

In order to address the deficiencies in the prior art and provide improved performance, a nebulizer and method are provided. According to a first aspect of the invention, a nebulizer is provided with a housing having an ambient air inlet and a chamber for holding an aerosol. An air outlet communicates with the chamber for permitting the aerosol to be withdrawn from the chamber. A fluid outlet and a pressurized gas outlet are in communication with the chamber where the pressurized gas outlet is located adjacent to the fluid outlet. In one preferred embodiment, the fluid outlet is preferably positioned at the opposite end of a nozzle cover from a fluid inlet, wherein the fluid inlet is capable of fluid communication with a reservoir. A diverter is positioned in the chamber in a fixed position relative to the pressurized gas orifice.

At least one portion of the fluid orifice is adjustable between a nebulizing position and a non-nebulizing position. As used in this specification, the term "fluid orifice" means either the fluid inlet or the fluid outlet and may be used interchangeably with these terms. The nebulizer may have an actuator piston connected with at least a portion of a nozzle cover to move all or part of the fluid orifice, or all or part of the fluid pathway between the reservoir of fluid and the fluid orifice. Additionally, a relief piston independently movable with respect to the actuator piston may be used to alleviate inhalation effort after an initial period of inhalation. In one embodiment, the fluid orifice is movable in response to a patient's breathing. In another embodiment, the fluid orifice is movable by moving a mechanical actuator by hand. In yet further embodiments, the diverter may be movable relative to the nebulizer housing, but fixedly positioned relative to either the pressurized gas orifice or fluid orifice.

According to another aspect of the invention, a method of providing a nebulized fluid to a patient includes providing a nebulizer having a diverter fixedly positioned with respect to a pressurized gas outlet in a chamber, a fluid reservoir in communication with the chamber, and an adjustable fluid pathway movably positioned to communicate fluid in the fluid reservoir with a fluid orifice in response to inhalation by the patient. Upon inhalation through an air outlet connected to the chamber, a position of the fluid pathway is adjusted with the force of the inhalation such that the fluid in the chamber is nebulized.

BRIEF DESCRIPTION OF SEVERAL VIEWS OF THE DRAWINGS

FIG. 1 is an elevational side view of a nebulizer according to one embodiment of the present invention.

FIG. 2 is an exploded top perspective view of the nebulizer of FIG. 1.

FIG. 3 is an exploded bottom perspective view of the nebulizer of FIG. 1.

FIG. 4 is a bottom perspective view of a nozzle cover suitable for use in the nebulizer of FIG. 1.

FIG. 5 is a cross-sectional view of the nozzle cover of FIG. 4.

FIG. 6 is a cross-sectional view of the nebulizer of FIGS. 1-3 in a non-actuated position.

FIG. 7 is a cross-sectional view of the nebulizer of FIG. 6 in a fully actuated position.

FIG. 8 is a cross-sectional view of the nebulizer of FIG. 1 illustrating air flow in a fully actuated position.

FIG. 9 is a cross-sectional view of an alternative embodiment of a diverter arrangement suitable for use with the nebulizer of FIG. 1.

FIG. 10 is a cross-sectional view of a second alternative embodiment of a diverter arrangement suitable for use with the nebulizer of FIG. 1.

FIG. 11 is a cross-sectional view of a third alternative embodiment of a diverter arrangement suitable for use with the nebulizer of FIG. 1.

FIG. 15 is a partial cross-sectional view of the nebulizer of FIG. 14 in an actuated position.

FIG. 16 is a partial cross-sectional view of the nebulizer of FIGS. 14-15 in a non-actuated position.

FIG. 22 is a cross-sectional view of the nebulizer of FIG. 21 in a non-actuated position.

FIG. 23 is a cross-sectional view of the nebulizer of FIG. 21 in an actuated position.

FIG. 27 is a cross-sectional view of a nebulizer illustrating a locking lever.

FIG. 28 is a sectional view of the nozzle and nozzle cover of FIG. 23.

FIG. 29 is a sectional view of the nozzle and nozzle cover of FIG. 22.

DETAILED DESCRIPTION OF THE PRESENTLY PREFERRED EMBODIMENTS

Figure 12:
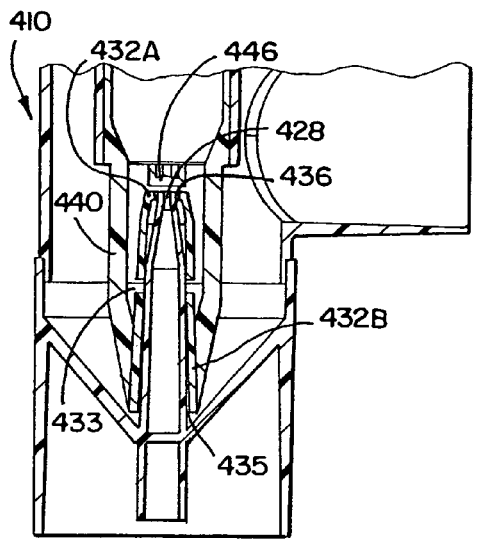
FIG. 12 is a partial cross-sectional view of an alternative embodiment of the nebulizer of FIGS. 1-8 in an actuated position.

A preferred embodiment of a nebulizer 10 for nebulizing a fluid is shown in FIGS. 1-3. As used in this specification, the term "fluid" includes, without limitation, a fluid comprising a medicine, whether in the form of an emulsion, suspension or solution, that can be nebulized into an aerosol. The embodiment of FIGS. 1-3 comprises a lid 11 attached to a housing 13 having a top portion 12, a cylindrical middle portion 14, and a bottom portion 16. An air outlet 18 extends from the cylindrical middle portion 14 of the housing 13. The air outlet 18 communicates with air in the chamber 20, defined by the inside of the cylindrical middle portion 14 of the housing, and is suited to receive a mouthpiece. In a preferred embodiment, the component parts of the housing may be formed of separate, multiple pieces of material that are connected together by welding, adhesives, threading, connector tabs. In an alternative embodiment the housing may be constructed of a single piece of material formed by an injection molding process. The housing may be constructed from a plastic material, such as polypropylene, polycarbonate or a polycarbonate blend, or a metal material. Any number of types of plastic or metal may be used to construct these parts of the nebulizer.

Referring to FIGS. 1-7, a pressurized gas inlet 22 extends into the chamber 20 through the bottom portion 16 of the housing. The opening 24 of the pressurized gas inlet 22 is designed to connect with a standard vinyl gas hose. Inside the chamber 20, the pressurized gas inlet 22 forms a nozzle 26 that tapers down to a pressurized gas orifice 28 having a predetermined diameter. In one preferred embodiment, the gas inlet 22 is coaxial with the cylindrical middle portion 14 and extends through the bottom wall 30 of the chamber 20.

A nozzle cover 32 is slideably mounted over the nozzle 26. As shown in FIGS. 4-5, the nozzle cover 32 is preferably a tapered tubular member having openings at either end. The nozzle cover 32 slides over the nozzle 26 of the pressurized gas inlet 22 to form at least one passageway 34 from an opening located near the bottom of the nozzle cover 32 to the top of the nozzle cover In alternative embodiments, the passageway may be formed by a spacing between the nozzle and nozzle cover, a groove 34 in the inner circumference of the nozzle cover, a groove in the outside of the nozzle, or a combination of grooves on the outside of the nozzle and inside of the nozzle cover. A fluid outlet is positioned adjacent the pressurized gas outlet 28 In one preferred embodiment, the fluid outlet 36 is an annular orifice defined by a gap between the inner diameter of the tip of the nozzle cover and the outer diameter of the tip of the nozzle. The tip of the nozzle cover 32 may include one or more stop pins 41 to limit the upward travel of the nozzle cover 32. Although a single annular orifice is shown, embodiments where the fluid outlet has other shapes, or comprises more than one discrete orifice positioned adjacent the pressurized gas orifice, are also contemplated. A fluid inlet 35 is preferably positioned at the opposite end of the nozzle cover 32. As shown in FIGS. 6-8, the fluid inlet is also an annular orifice and is defined by a gap between the inner diameter of the bottom of the nozzle cover 32 and the outer diameter of the base of the nozzle 26.

An embodiment is also contemplated with fluid pathways that are completely enclosed within the thickness of the nozzle cover such as one or more tunnels bored from, or molded in, the bottom of the nozzle cover extend some or all of the distance up to the opening at the top of the nozzle cover. Further, an alternative embodiment may consist of an array of one or more discrete tubes connected in a ring around the pressurized gas outlet 28, where each of the tubes provides a passageway from the fluid reservoir 80 to a respective point adjacent the pressurized gas outlet 28.

In the embodiment of FIGS. 1-8, the entire nozzle cover 32 is attached to, or integrally molded with, an actuator piston 38. In one embodiment, the nozzle cover includes one or more integrally formed arms 40 that connect to the bottom portion 42 of the circumferential flange 44 of the actuator piston 38. Any number of arms 40 may be utilized.

A diverter 46 is preferably attached to, or integrally molded with, the inside of the nebulizer 10. As shown in FIG. 3, a support beam 48 connects the diverter 46 to an inner cylindrical flange 60 in the middle portion 14 of the nebulizer. Preferably, the diverter 46 has a flat surface having a predetermined area and is positioned at a fixed distance $h_1$ from the gas orifice 28. In one preferred embodiment, $h_1$ is approximately 0.75 millimeters (mm) and the width of the diverter is approximately 4.5 mm. The surface is also preferably aligned parallel to the surface of the tip of the nozzle 26 and perpendicular to the flow of pressurized gas through the pressurized gas orifice 28.

Any of a number of configurations for fixing the position of the diverter with respect to the pressurized gas orifice are contemplated. For example, the cylindrical flange 160 may extend further into the chamber 120 so that the diverter 146 and support arm 148 are attached or molded further from the bottom of the cylindrical flange 160 as shown in the embodiment illustrated in FIG. 8. In FIG. 9, an embodiment is shown where the diverter 246 is attached to a support 248 directly connected to the wall of the middle portion of the housing. A shorter cylindrical flange 260 provides clearance for the support 248. Alternatively, as shown in FIG. 10, the diverter 346 may be attached or molded to the lid 311 of the nebulizer via an extension arm 348. In other alternative embodiments, the diverter may be movable with respect to the pressurized gas orifice or may be movable with the pressurized gas orifice such that the pressurized gas orifice and diverter move together independently of the fluid orifice. Another suitable diverter configuration is disclosed in U.S. Pat. No. 6,044,841, the entire disclosure of which is incorporated herein by reference.

Referring again to FIGS. 1-8, the upper portion 12 of the housing 13 forms a cylindrical extension with an open proximal end 52 and a partially closed distal end 54. The distal end 54 has an annular ledge 50 surrounding an opening 58 into the chamber 20. The annular ledge 50 defines at least one air inlet opening 56 and preferably eight air inlet openings distributed along its circumference. Each air inlet opening 56 is located toward the outer periphery of the distal end 54 of the upper portion 12 such that air outside of the nebulizer is primarily directed against an actuator piston 38 covering the air inlet opening 56 during the patient's initial inhalation. Preferably, the nebulizer is configured such that a gap exists between the air inlet opening and the actuator piston when the nebulizer is in a non-actuated state.

The opening 58 at the distal end 54 connects with a chimney, or cylindrical flange 60, extending down into the upper portion of the chamber 20. The cylindrical flange 60 is preferably of a diameter suited to slideably receive the cylindrical extension 62 of the actuator piston 38 that extends downward into the chamber 20. The cylindrical extension 62 is positioned substantially coaxially within the cylindrical flange 60 and acts as a vertical guide for the actuator piston 38. The open proximal end 52 of the upper portion 12 of the housing 13 has a diameter suited to receive the lid 11. The lid 11 may be threaded, snap-fit, friction-fit, molded or welded to the upper portion 12 of the housing 13. The middle portion 14 of the housing 13 is preferably manufactured of a clear plastic so that a caregiver can see the actuator piston and determine if the nebulizer is actuated.

The interior of the upper portion 12 is suited to slideably receive the actuator piston 38 and a relief piston 62, and to receive a biasing means 64 such as a plastic or metal spring. The actuator piston 38, as shown in FIGS. 2-3 and 6-8, includes an outer annular rib 66 with an outer diameter slightly less than the inner diameter of the upper portion 12 of the housing 13 to allow the actuator piston 38 to slide up and down within the upper portion 12. A center hole 68 is bounded by the cylindrical extension 62 that extends both down into the chamber 20 through the opening 58 and, in the opposite direction, a short distance into the upper portion 12. At least one air inlet 72 is located in the actuator piston 38 adjacent to the center hole 68 that allows entrained air received from air inlets 56 in the housing to travel through the actuator piston and against the underside of the relief piston 62. As described in more detail below, the negative pressure created above the relief piston 62 during inhalation preferably creates a force sufficient to move the relief piston 62 away from the actuator piston and allows increased air flow to the patient through openings 72 in the actuator piston 38. The actuator piston also includes at least one arm 40 or other structure connecting the nozzle cover 32 or part thereof to the bottom portion of the actuator piston cylindrical extension 62. The arm can be attached (i.e. friction fit, welded or glued), or integrally molded to the extension 62.

Referring to FIGS. 2-3, the relief piston 62 also has an annular shape defining a central opening 74. An inner annular rib 46 extends upward from an inner diameter of the relief piston 62 and an outer annular rib 78 extends upward from an outer diameter of the relief piston. The central opening 74 has a diameter slightly larger than the portion of the cylindrical extension 62 extending up from the actuator piston's center hole 68. The outer diameter of the relief piston 62 is slightly less than the inner diameter of the actuator piston's raised annular rib 38 to allow the relief piston to slideably move between the ribs of the actuator piston. The outer diameter of the outer annular rib on the relief piston is also less than the inner diameter of the lid 11. Although the embodiment of FIGS. 2-3 illustrates a relief piston, in another embodiment the nebulizer includes only the actuator piston and not the relief piston.

A biasing means 64, such as a plastic or metal spring, is positioned adjacent the top of the relief piston 62. The biasing means 64 has a predetermined spring force that is designed to hold the pistons 38, 62 down during an absence of inhalation, but that will be overcome once sufficient negative pressure is created by a patient's inhalation effort. In a preferred embodiment, one end of the biasing means 64 rests against the retainer lid 11 and the other end against relief piston 62 between the inner and outer annular ribs 46, 78. Other biasing means, such as a flexible membrane or a set of oppositely charged magnetic materials, may also be used. Additionally, the biasing means may consist of extra weights added to the relief piston and actuator piston, or the weight of the relief and actuator pistons by themselves, rather than a spring, so that gravity may be used to provide the necessary biasing force keeping the pistons against the air inlets 56, 72 in a resting or exhalation position.

The bottom portion 16 of the housing 3 is used as a fluid reservoir 80. The fluid reservoir 80 preferably holds a fluid. In one embodiment, the fluid may comprise medication used to alleviate respiratory ailments such as asthma and chronic obstructive pulmonary disease. The fluid reservoir 80 is bounded by a wall 30 that slopes down towards the bottom of the nozzle 26. Gravity urges the fluid in the reservoir toward the passageway 34 defined by the nozzle and nozzle cover. Both the cylindrical middle portion 14 of the housing 13 and bottom portion 16 of the housing 13 are preferably constructed from a transparent plastic to allow a caregiver to monitor medication levels in the nebulizer. When in a nebulizing position, the passageway 34 guides the fluid from the fluid reservoir to the fluid outlet 36.

Various alternative fluid reservoirs can be used in the nebulizer 10 For example, as is disclosed in U.S. Pat. No. 5,823,179, the reservoir may be formed of at least two portions: (1) an upper portion which is relatively shallow and wide with a diameter approximately the same as that of the chamber; and (2) a lower portion that is relatively narrow, but relatively deep. In this embodiment, the lower portion of the reservoir is wider than the outer diameter of the nozzle cover. This alternative embodiment can also be modified to include a third intermediate portion located between the upper and lower portions. The entire disclosure of U.S. Pat. No. 5,823,179 is incorporated herein by reference.

Referring to FIGS. 6-8, the operation of the nebulizer is described below. In the non-actuating state shown in FIG. 6, when a patient is exhaling or no longer inhaling, the biasing means 64 pushes against the inside of the lid 11 and down against the relief piston 62. The relief piston 62 presses against the actuator piston 38 which, in turn, keeps the nozzle cover 32 a distance $h_2$ away from the diverter and against the nozzle 26. Thus, the fluid outlet 36 is positioned away from the pressurized gas orifice and, therefore, there is insufficient negative pressure to draw up the fluid from the reservoir through the passageways.

Pressurized gas is continuously introduced into the chamber via the pressurized gas orifice 28 and is deflected radially outward from the gas orifice in a 360° pattern by the deflector 46. In the non-actuated position, the flow of gas fanning out over the annular fluid outlet is at a sufficient distance $h_2$ from the annular fluid outlet that no nebulization takes place. Additionally, the force of the biasing member against the relief and actuator pistons closes the air inlets 72, 56 and keeps air and any nebulized substance in the chamber 20 from escaping through the air inlets. In one embodiment, $h_2$ is approximately 2.0 mm when $h_1$, the fixed distance between diverter and nozzle, is 0.75 mm. Other ratios of $h_2$ and $h_1$ may be utilized to take into account changes in parameters such as the viscosity of the fluid in the reservoir and the velocity of the pressurized gas entering the chamber.

When a patient begins inhaling through the air outlet 18, the force of the patient's inhalation lowers the pressure in the chamber and creates a negative pressure above the pistons causing both the actuator piston and relief piston to simultaneously lift away from the annular wall of the upper portion of the housing. The nozzle cover 32, rigidly attached to the actuator piston through the cylindrical extension and arms, moves up the pressurized gas nozzle until the fluid outlet reaches the low pressure zone created by the continuous flow of gas diverted by the diverter. In order to maintain the fluid outlet at the appropriate position during inhalation, upward movement of the actuator piston is preferably limited by contact of the outer annular rib with the edge of the lid 11. Alternatively, other points of contact may be used to limit the maximum upward movement of the nozzle and actuator piston For example, the plurality of stops 41 on the upper edge of the nozzle cover 32 shown in FIGS. 4 and 5 may be arranged around the perimeter of the tip of the nozzle cover so that motion of the nozzle cover is limited when these stops contact the diverter.

In the nebulizing position (FIGS. 7 and 8) the low pressure zone created over the annular fluid outlet by the gas fanning out against the deflector and over the annular orifice, along with a capillary effect, draws the fluid from the reservoir 80 through the passageways 34 and into the stream of pressurized gas. The fluid is aerosolized and drawn out through the air outlets 18 and a mouthpiece (not shown) into the patient's respiratory system. After the nebulizer has already initiated nebulization of the fluid, and while the patient is continuing to inhale and increase the negative pressure in the chamber, the relief piston will separate from the actuator piston thereby allowing more ambient air to be entrained in the cylinder and chamber As illustrated in FIG. 7, the edge 15 of the lid 11 limits motion of the actuator piston 38, but the smaller diameter relief piston 62 is not restricted by contact with the edge of the lid and will separate from the actuator piston after the initial period of the patient's inhalation.

Although nebulization has already started as soon as the actuator piston has lifted the nozzle cover to the appropriate spacing from the diverter, continued inhalation causes the relief piston to separate from the actuator piston. Separation of the relief piston from the actuator piston uncovers additional air inlets in the actuator piston and has the effect of increasing air flow into the nebulizer and reducing the resistance to inhalation. FIG. 8 illustrates the flow path 71 of ambient air from outside the nebulizer through the inlets 56 in the housing 13 and inlet 72 in the actuator piston 38. Ambient air continues down the central portion of the nebulizer through the cylindrical flange 60 and cylindrical extension 62 where nebulized fluid is gathered and drawn through the air outlet 18. In alternative embodiments, the upper portion 12 of the housing may include internal protrusions or a flange positioned to stop upward movement of the actuator piston and maintain a proper spacing between the annular orifice and the diverter during nebulization. An advantage of the fixed diverter embodiment shown in FIGS. 1-8 is that the inhalation effort necessary to actuate the nebulizer is substantially unaffected by the force of the pressurized gas impacting on the diverter.

Upon exhalation, the negative pressure in the chamber is replaced with a positive pressure such that the force of the biasing member against the relief and actuator pistons closes the air inlets and again moves the nozzle cover away from the low pressure zone generated by the pressurized gas inlet and diverter. Continued exhalation directs exhaled air through a relief valve on the mouthpiece (not shown) connected to the air outlet to direct exhalation away from the nebulizer. Any of a number of commonly available relief valves may be used with the presently preferred embodiment. A suitable mouthpiece and relief valve are illustrated in U.S. Pat. No. 6,044,841, the entire specification of which is incorporated herein by reference.

Although preferably operated by breath actuation, the nebulizer 10 may also be manually actuated. As shown in the embodiment of FIG. 11, the nebulizer 310 may include a manual actuating member 301 connected with, integral to, or capable of contact with the actuator piston 338 and extending out of the upper portion 312 of the housing 313 through an air inlet 356 or other opening. In FIG. 11, the manual actuating member 301 is integrally formed with the actuator piston 338. The actuating member 301 permits a caregiver or patient to move the actuator piston by hand, and thus move the nozzle cover, so that the nebulizer initiates nebulization. Although the manually actuable nebulizer 310 is illustrated with a diverter that is integrally formed with the lid, any of the other diverter or nozzle configurations disclosed herein, or their equivalents, may be used.

Figure 13:
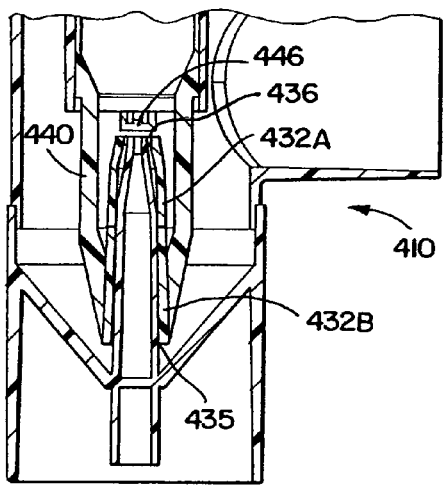
FIG. 13 is a partial cross-sectional view of the nebulizer of FIG. 12 in a non-actuated position.
Figure 14:
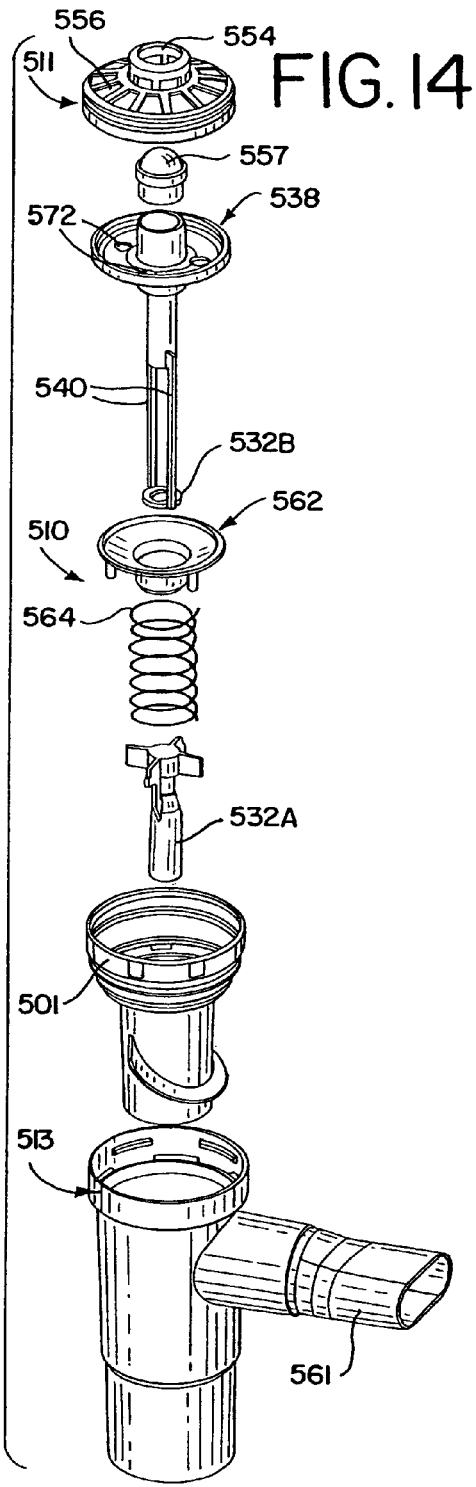
FIG. 14 is an exploded side elevational view of a second alternative embodiment of the nebulizer of FIGS. 1-8.

An alternative embodiment of a nebulizer 410 is illustrated in FIGS. 12 and 13. Here, the nozzle cover consists of two portions. A first portion 432A is fixed at the top of the gas nozzle 426 so that the pressurized gas inlet 428, diverter 446 and annular orifice of the fluid outlet 436 are all fixedly positioned with respect to one another at a spacing suitable for nebulization. The second portion 432B is attached to the actuator piston with arms 440 and is moveable a predetermined distance up and down the axis of the gas nozzle so that the annular orifice of the fluid inlet 435 moves with the actuator piston. As with the nozzle cover of the embodiment in FIGS. 1-8, one or more fluid pathways are defined by spacing between the gas nozzle and nozzle cover, grooves in the nozzle cover, grooves in the gas nozzle, or a combination of these options.

In the non-actuating position, the second portion 432B is separate from the first portion 432A such that a gap 433 of a predetermined distance exists between the two portions as shown in FIG. 12 As a result of the gap, the first portion 432A of the nozzle cover does not contact the fluid reservoir and there is no continuous fluid pathway between the fluid orifices, in other words no pathway from the reservoir and fluid inlet 435 to the fluid outlet 436, so that no fluid may reach the fluid outlet. In the actuating-position, the second portion is moved up until it mates or abuts with the first portion as shown in FIG. 13. The two portions 432A, 432B cooperate to form at least one continuous fluid pathway between the fluid outlet and the reservoir The continuous fluid pathway permits the negative pressure over the fluid outlet to draw fluid from the reservoir and initiate nebulization. Similar to the embodiment of FIGS. 1-8, the embodiment of FIGS. 12-13 may utilize both the actuator and relief pistons, or it may only include the actuator piston.

Another alternative embodiment of the nebulizer is illustrated in FIGS. 14-16. In this embodiment, the nozzle cover has a fixed first portion 532A and a movable second portion 532B. The first portion 532A is fixed at the top of the gas nozzle 526 so that the pressurized gas inlet 528, diverter 546 and annular fluid outlet 536 are all fixedly positioned with respect to one another at a spacing suitable for nebulization. Preferably, the diverter 546 is connected with, or integrally formed with a portion of the housing 513 or a chimney insert 501 connected with the housing 513.

Unlike the embodiment of FIGS. 12 and 13, the nebulizer 510 is in the actuated position when the two portions 532A, 532B are separated. Preferably, the first portion 532A extends down into the reservoir and defines at least one fluid pathway to the annular orifice. The second portion 532B defines a collar for blocking the fluid inlet 535 at the first portion 532A. In one embodiment, the fluid inlet 535 may be an annular orifice defined by the space between the first portion and the gas nozzle 526. In another embodiment, the fluid inlet 535 may be one or more separate fluid openings that are part of, or connected to, the base of the first portion 532A. Preferably, the second portion is movable between a first position where any fluid pathway is substantially shut off and a second position where the fluid inlet is open and the fluid pathway is open. When the nebulizer is in the non-actuated state (FIG. 15), the second portion abuts, or mates with, the first portion. In the actuated position (FIG. 16), the second portion 532B is separated from the first portion 532A and nebulization can occur.

In order to achieve the separation of the first and second portions 532A, 532B, movement of the actuator 538 and relief 562 pistons should be opposite that of the actuator and relief pistons illustrated in the embodiment of FIGS. 1-8. Specifically, the pistons should move from the top of the nebulizer toward the bottom during inhalation so that the second portion of the nozzle cover will move down and away from the first portion. As shown in FIGS. 14-16, the nebulizer 510 has the relief piston 562 coaxially positioned around a portion of the actuator piston 538. A biasing member 564 holds the actuator and relief pistons 538, 562 against the lid 511 so that the air inlets 556 in the lid 511 are covered by the pistons. The lid 511 mates with the chimney insert 501 connected to the housing 513, and the upper portion of the chimney insert 501 provides a ledge that limits the downward movement of the actuator piston 538 after a patient begins to inhale and actuates the nebulizer (see FIG. 16). Thus, when the patient inhales through the mouth piece 561, a negative pressure pulls both the actuator and relief pistons down and moves the second portion of the nozzle cover 532B to permit fluid to reach both fluid orifices (i.e. the fluid inlet 535 and the fluid outlet 536).

Figure 17:
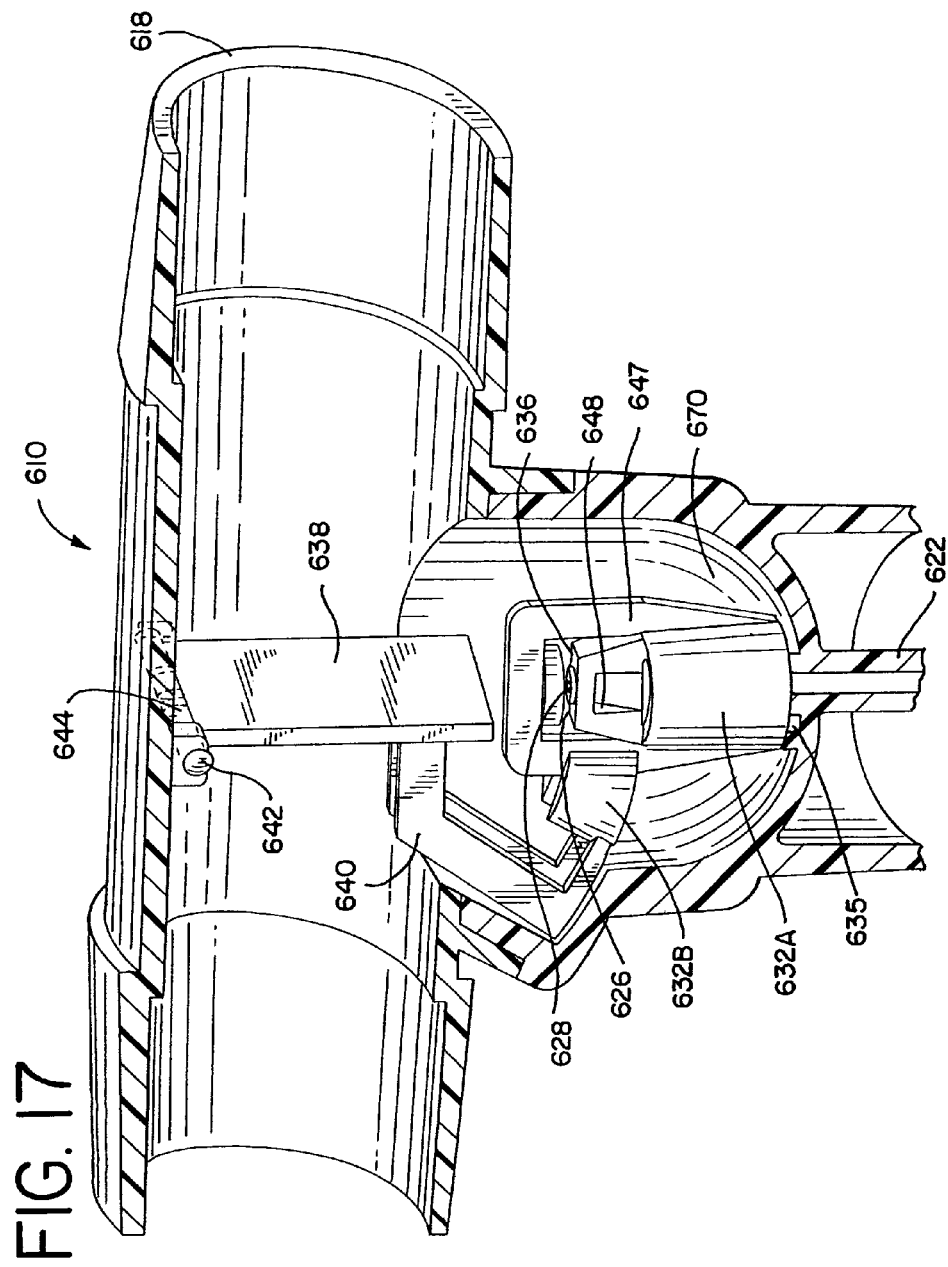
FIG. 17 is a cross-sectional view of a third alternative embodiment of the nebulizer of FIGS. 1-8 in a non-actuated position.

Additional inhalation draws the relief piston 562 away from the actuator piston 538 so that air from the inlets 556 can also flow through openings 572 in the actuator piston and relieves the inhalation effort. Upon exhalation, the biasing member force returns the pistons 538, 562 to a non-nebulizing position and exhaled air is directed through a one-way valve 563 in the mouthpiece 561. This embodiment of the nebulizer may also be manually actuated by pressing down on a manual actuator 557 extending through a central opening 559 in the lid 511. One suitable nebulizer piston configuration is illustrated in U.S. Pat. No. 6,044,841, the entire disclosure of which is incorporated herein by reference. In similar fashion, the downward moving piston configuration may be used with a nozzle cover that is suspended above, or against, the diverter so that inhalation effort would move the actuator piston and attached nozzle cover down to complete the fluid pathway and place the fluid orifice in the low pressure zone created by the continuous flow of pressurized gas against the diverter. All or a portion of the nozzle cover may be connected with the actuator piston in this downward piston motion alternative embodiment.

Another alternative embodiment of the nebulizer is illustrated in FIGS. 17 and 18. In this embodiment, the nebulizer 610 has a housing with a horizontal section 612 and a vertical section 614. The horizontal section has an air inlet 616 for receiving a supply of air and an air outlet 618 where a patient inhales nebulized fluid. The vertical section 614 defines a fluid reservoir 620 for holding the fluid. A pressurized gas inlet 622 extends into the chamber 624 through the bottom portion of the vertical section 614. Inside the chamber 624, the pressurized gas inlet 622 forms a nozzle 626 that tapers down to a pressurized gas orifice 628 positioned opposite a diverter 646. The diverter 646 is preferably fixedly positioned by support arms 647 to the housing and maintained at a fixed distance from the gas orifice. As shown, the diverter is attached to a fixed portion 632A of the nozzle cover. The fixed portion 632A of the nozzle cover is attached to the vertical section 614 by one or more nozzle cover supports 633. The fixed portion of the nozzle cover defines a fluid inlet 635, which may comprise one or more openings near the bottom of the reservoir 620, and defines a fluid outlet 636, which may be an annular orifice, with the tip of the pressurized gas nozzle 626.

As illustrated in FIG. 17, a movable portion 632B of the nozzle cover is connected by arms 640 to a vane 638 pivotally attached with an axle 642 mounted in a bracket on the horizontal section 612 of the nebulizer 610. A biasing member, such as a torsion spring 644 positioned on the axle 642, urges the movable portion 632B of the nozzle cover away from the pressurized gas nozzle 626 so that, at rest or during exhalation, there is a gap 648 that prevents fluid from reaching the fluid outlet 636. Accordingly, as illustrated in FIG. 16, no nebulization takes place during exhalation when the movable portion of the nozzle cover is held away from the fixed portion and the pressurized gas nozzle. When a patient inhales at the outlet 618, the flow of air through the horizontal section 612 draws the vane toward the air outlet 618. The movable portion 632B of the nozzle cover pivots with the vane 638 and covers the gap 648 so that a complete fluid path is formed between the fluid orifices from the fluid inlet 635 at the reservoir 620 to the fluid outlet 636 as shown in FIG. 17. As explained above for the other embodiments, the continuous flow of pressurized gas from the pressurized gas orifice against the fixed diverter 646 creates a low pressure region above the fluid outlet so that fluid is drawn up along the fluid pathway, or pathways, between the nozzle cover and nozzle. This fluid is then nebulized in the pressurized gas flow.

Figure 18:
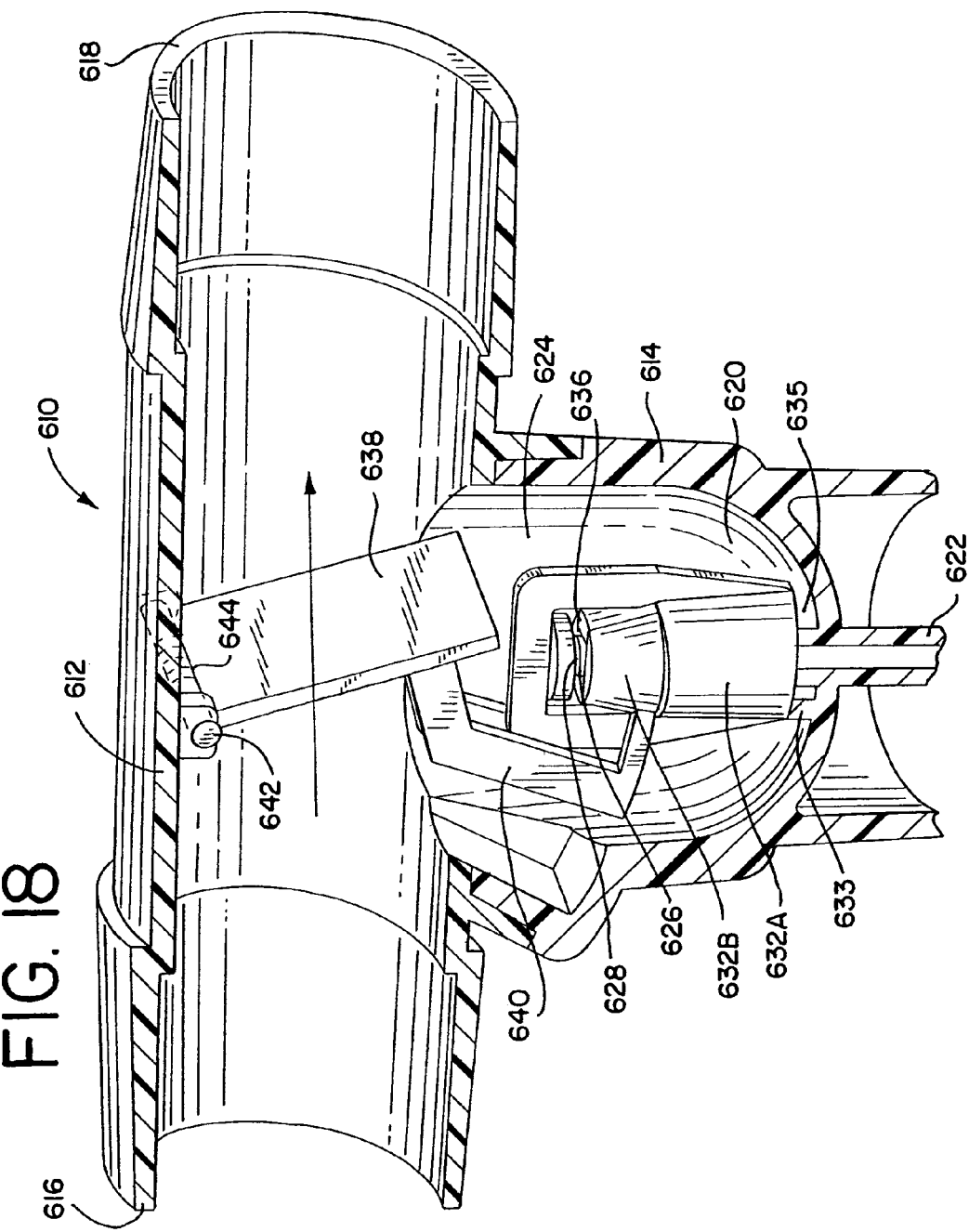
FIG. 18 is a partial cross-sectional view of the nebulizer of FIG. 17 in an actuated position
Figure 19:
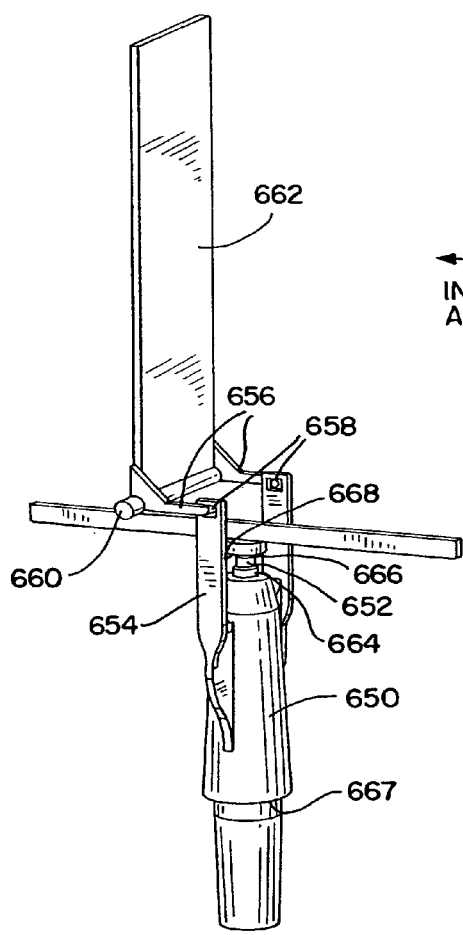
FIG. 19 is an alternative nozzle cover and vane assembly, in a non-actuated position, for use in the nebulizer of FIGS. 17-18.
Figure 20:
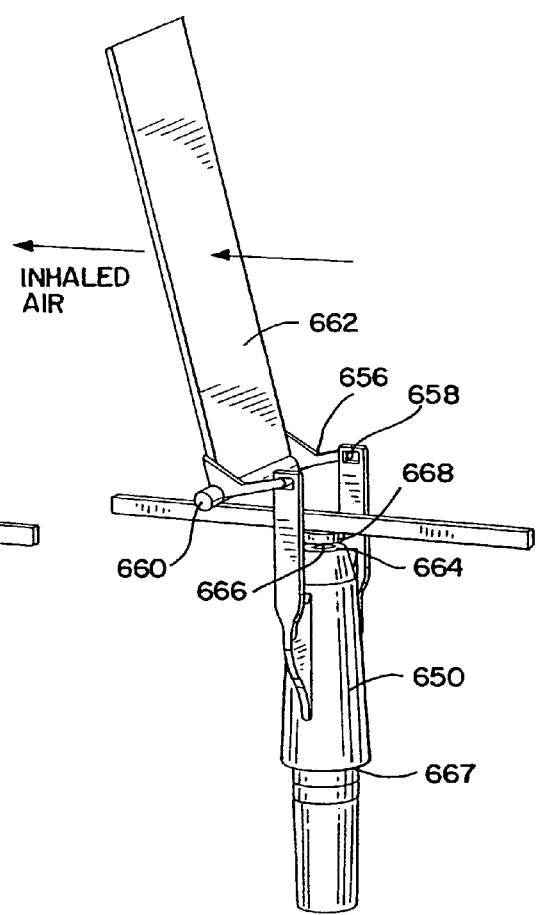
FIG. 20 is an alternative nozzle cover and vane assembly, in an actuated position, for use in the nebulizer of FIGS. 17-18.

Illustrated in FIGS. 19 and 20 is an alternative embodiment of the vane and nozzle cover assembly for use with the housing having the horizontal 612 and vertical 614 sections as shown in FIGS. 17 and 18. The nozzle cover 650 is movably mounted relative to the gas nozzle 652. The gas nozzle is preferably attached to the vertical section 614 of the nebulizer. A pair of arms 654 attached to the nozzle cover 650 are linked to rocker arms 656 at linkage points 658. The rocker arms 656 are attached to an axle 660 that pivots about its axis in response to movement of a vane 662. The vane 662 is also attached to the axle 660. The axle 660 is preferably rotatably mounted in the wall of the vertical or horizontal section of the nebulizer.

FIG. 19 shows the vane 662 and nozzle cover 650 in a non-actuated position. In the non-actuated position, the nozzle cover 650 is held down against the gas nozzle 652 such that the fluid outlet 664 is positioned away from the low pressure region created by the flow of pressurized gas from the pressurized gas orifice 666 against the diverter 668. The diverter 668 is preferably attached to a support 670 that is fixedly attached to the housing of the nebulizer. Alternatively, and/or additionally, the nozzle cover 650 may be configured to sufficiently close off the fluid inlet 667 so that substantially no fluid may flow into the fluid passage or passages (not shown) between the fluid orifices (inlet 667 and outlet 664) when the nebulizer is in the non-actuated position. The weight of the nozzle cover 650, or the biasing force applied by a biasing member such as a spring, may keep the nozzle cover in the non-actuated position at rest and during exhalation.

Referring to FIG. 20, when a patient inhales through the nebulizer, the flow of inhaled air causes the vane to move. The vane moves by pivoting about the axis of the axle. The movement of the axle causes the rocker arms to lift up the nozzle cover via the linkage points 658 and arms 654. The movement of the nozzle cover moves the location of the fluid outlet 664 to a desired position relative to the diverter 668 such that fluid may be drawn up through the fluid inlet 667 from the fluid reservoir along the one or more fluid pathways. Various types of stops (not shown) may be used to limit the movement of the nozzle cover after it reaches the actuating position. For example, as discussed previously, protrusions may be fabricated, or attached, to the top of the nozzle cover keep the proper spacing between the nozzle cover and diverter during actuation. Alternatively, one or more stops may be fabricated, or attached, to the interior of the nebulizer such that the vane 662 cannot pivot about the axle any farther than the optimum actuation position.

In alternative embodiments, the vane 638, 662 may be constructed of a flexible material that is configured to flex with a patients inhalation and exhalation rather than pivoting about a point. Also, different portions of the nozzle and/or nozzle cover may be movably mounted to swing with the vane and form the fluid pathway or a fluid orifice during inhalation. Further, a movable collar may be used to block the fluid inlet 667 or outlet 664 in another alternative configuration capable of actuating the nebulizer in coordination with a patient's breathing.

Figure 21:
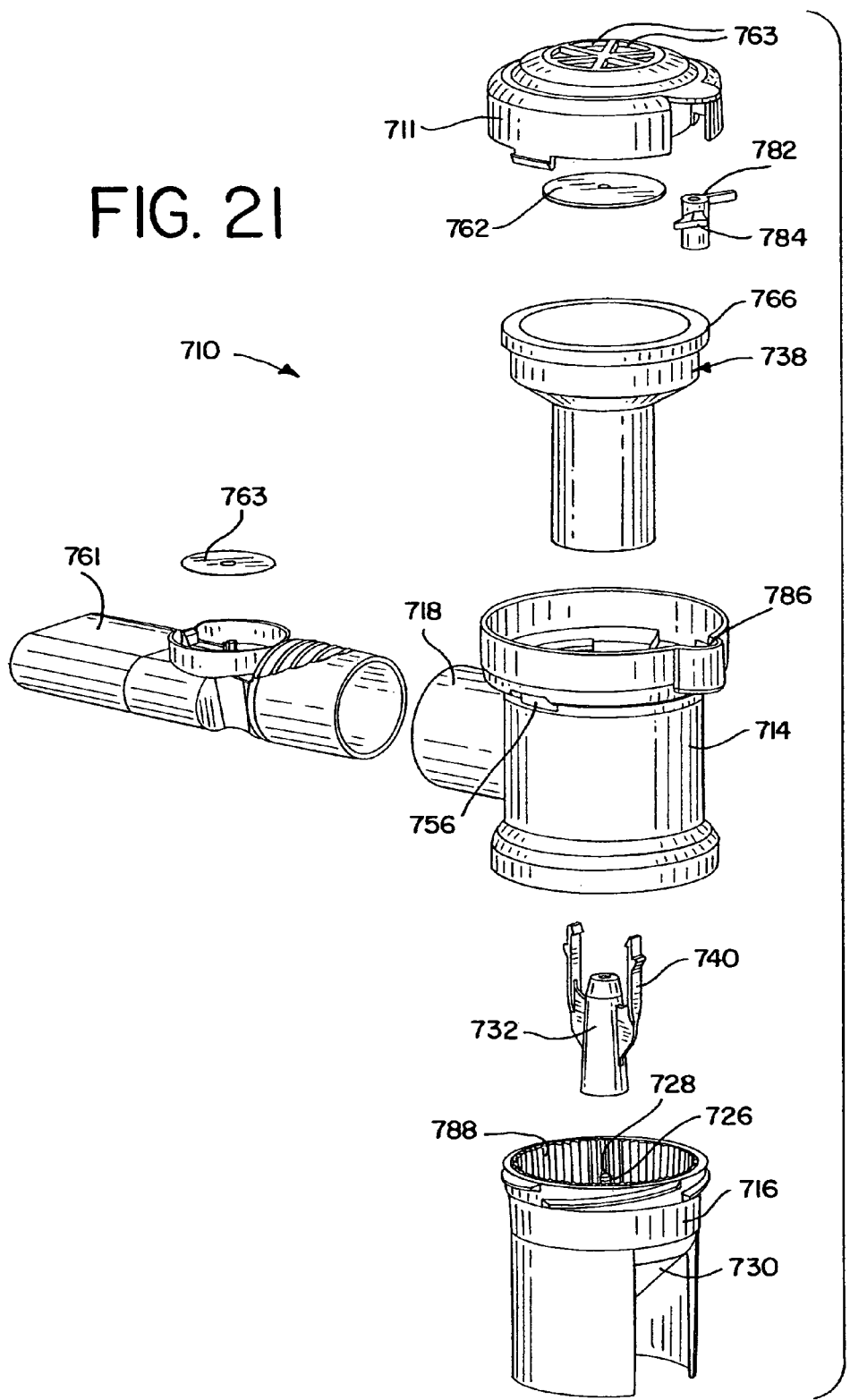
FIG. 21 is an exploded view of a fourth alternative embodiment of the nebulizer of FIGS. 1-8.

In the embodiment of FIGS. 21-27, a nebulizer 710 is shown with a relief piston 762 separately mounted to the lid 711 and the actuator piston slidably movable between the lid 711 and the inner cylindrical flange 760 in the central portion 714 of the housing. A diverter 746 is connected to the lower portion of the inner cylindrical flange 760 and maintained at a fixed distance from the pressurized gas orifice 728 on the pressurized gas inlet 726. A nozzle cover 732 is attached to the actuator piston 738 by arms 740 integrally formed with the nozzle cover. A bottom portion 716 of the nebulizer 710 defines a fluid reservoir 780 for holding a fluid to be nebulized. As shown in FIGS. 21-23, the bottom portion 716 may be threadably attached to the middle portion 714 of the nebulizer.

Figure 24:
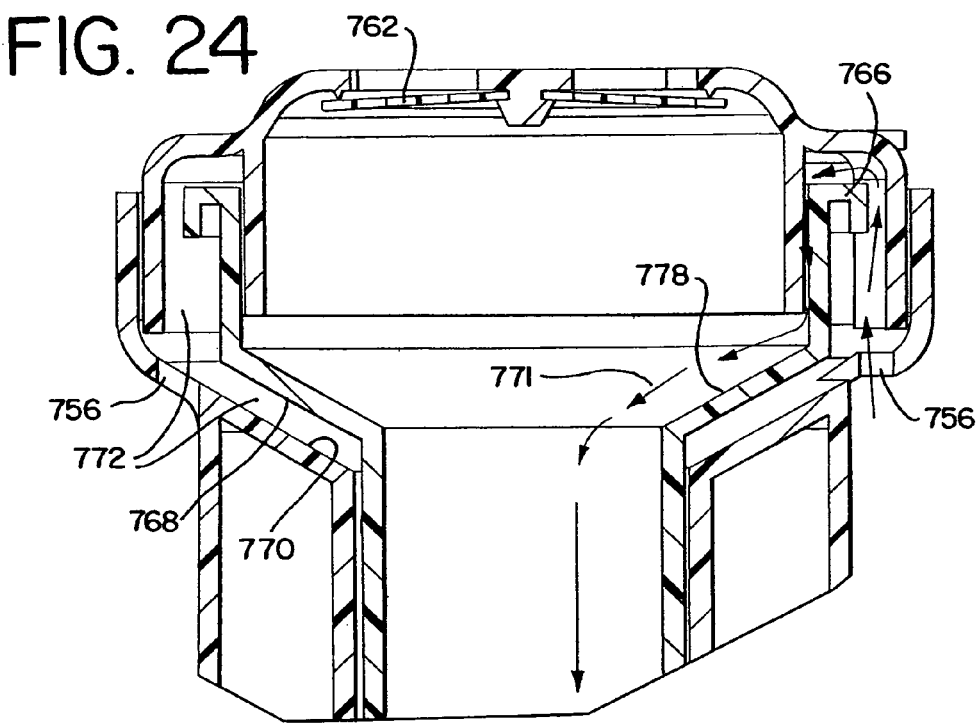
FIG. 24 is a sectional view of the nebulizer of FIGS. 21-23.
Figure 25:
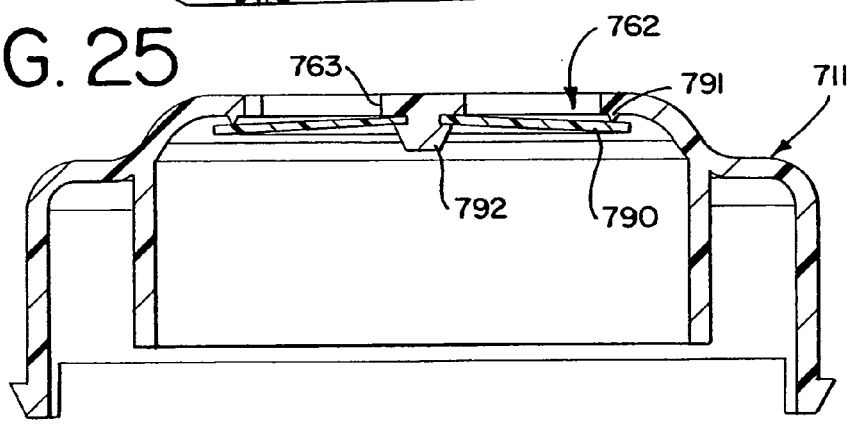
FIG. 25 is a lid and relief piston assembly suitable for use in the nebulizer of FIG. 21.
Figure 26:
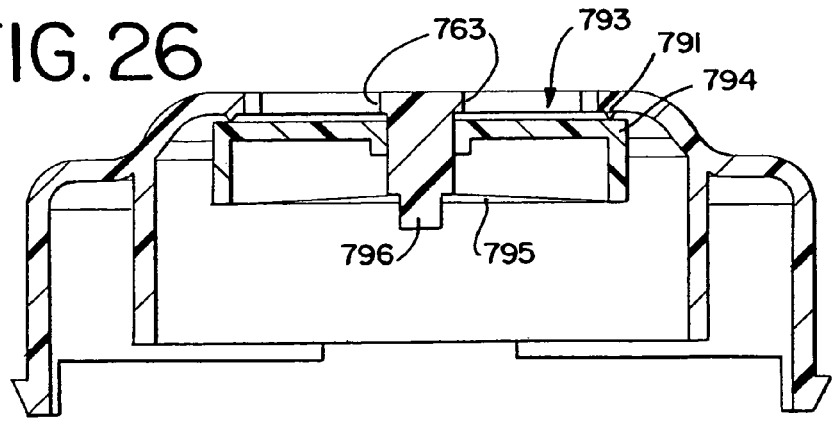
FIG. 26 is an alternative lid and relief piston assembly for use in the nebulizer of FIG. 21.
Figure 30:
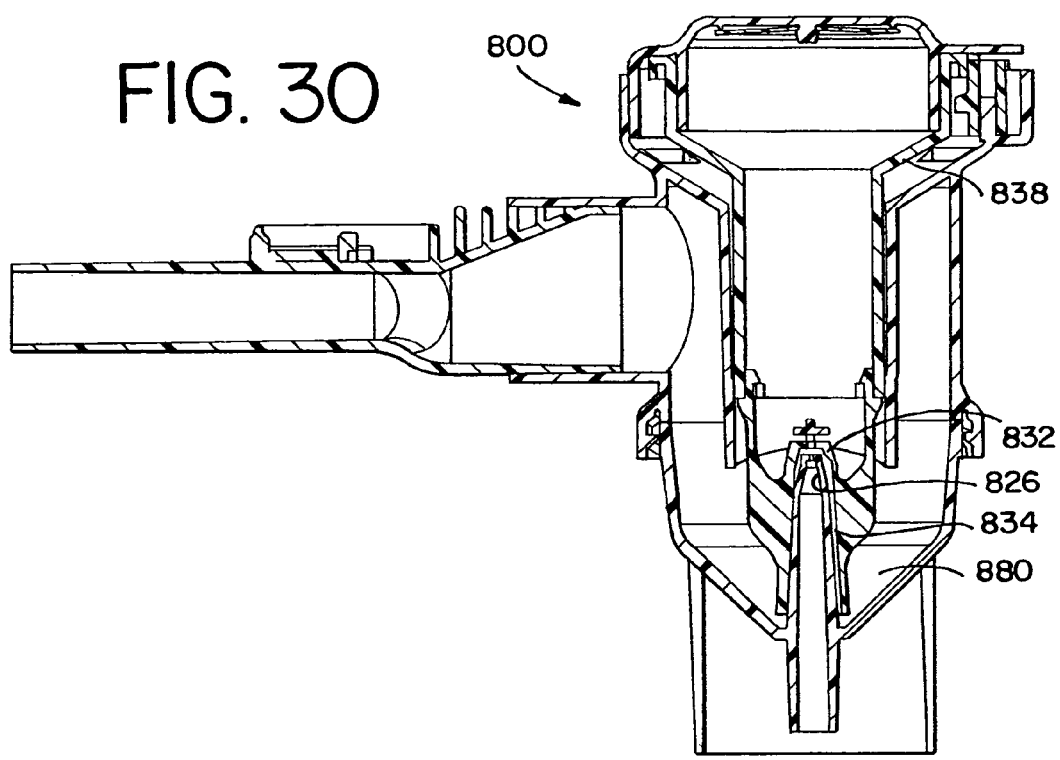
FIG. 30 is a cross-sectional view of an alternative embodiment of the nebulizer of FIGS. 21-24 with a gas nozzle and nozzle cover arranged in internal mixing configuration.
Figure 31:
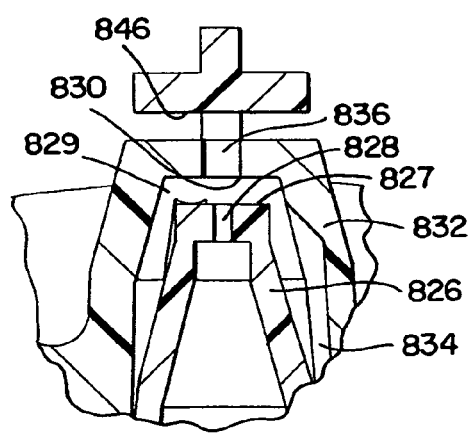
FIG. 31 is a sectional view of the gas nozzle and nozzle cover in the nebulizer of FIG. 30 in an actuated position.
Figure 32:
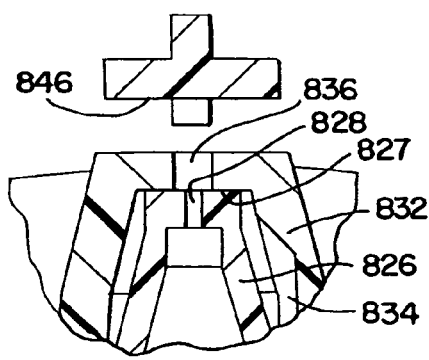
FIG. 32 is a sectional view of the gas nozzle and nozzle cover in the nebulizer of FIG. 30 in a non-actuated position.

In operation, the nebulizer 710 is in a non-actuated state when at rest (FIG. 23) or during a patient's exhalation, and in an actuated state during a patient's inhalation (FIG. 21). Referring to FIGS. 22 and 24, when a patient inhales through the mouthpiece 761 and draws air from the chamber 720, ambient air is pulled through the air inlets 756 in the middle portion 714 of the housing and into a chamber 772 between the outside surface 768 of the actuator piston 738 and the inside surface 770 of the middle portion 714 of the housing. The ambient air is then drawn up over the lip 766 of the actuator piston, down between the inner surface 778 of the actuator piston and the inner extension 746 of the lid 711, and into the chamber 720 as shown by flow arrows 771. As best shown in FIG. 23, this air flow raises the actuator piston 738 up and moves the nozzle cover 732 up so that the fluid outlet 736 is raised to a nebulizing position and the fluid pathways 734 defined between the nozzle cover 732 and the pressurized gas nozzle 726, or the fluid inlet 735, are not interrupted. Once the nozzle cover has moved to the actuated position, shown in FIG. 23, the fluid in the fluid reservoir 780 is drawn into the fluid inlet 735, up the fluid pathway and out the fluid outlet 736, entrained against the fixed diverter 746 and aerosolized. As inhalation continues to increase the negative pressure in the chamber, the relief piston 762 will begin to open and allow more ambient air in through openings 763 in the lid.

Upon exhalation, the relief piston 762 will shut the openings in the lid to restore the original pressure in the housing. The actuator piston 738 will lower to its rest position and move the fluid outlet away from the low pressure zone created by the pressurized gas impacting the fixed diverter 746. Any air exhaled by the patient will preferably pass through a one-way valve 763 on the mouthpiece 761 and not enter the air outlet 718 of the nebulizer. Although the air inlets 756 are shown underneath the periphery of the middle portion 714 in FIGS. 21 and 24, the air inlets can be located in any position that will expose the outside surface 768 of the actuator piston 738 to ambient air. Additionally, in order to increase the performance of the nebulizer in low pressure/low flow situations, the area of the outside surface 768 exposed to ambient air may be increased.

In one preferred embodiment, if the continuous pressurized gas flow into the chamber 720 from the pressurized gas inlet 728 is at a rate of 8 Liters/minute (L/min), the actuator piston 738 will respond to the inhalation once the inhalation rate exceeds the 8 L/min and generates a negative pressure in the range of 0.5 to 1.0 centimeters $H_2O$. Nebulization should begin once the initial inhalation has moved the actuator piston up into the actuation position. The force initially keeping the actuator piston in the non-actuated state may be the weight of the actuator piston or may be supplied by any of a number of biasing members. As the patient continues inhaling and the negative pressure increases to approximately 1.0 centimeters $H_2O$, the relief piston 762 opens. The relief piston is preferably configured to increase the amount of additional ambient air provided to the chamber as the patient's inhalation increases to keep the negative pressure from rising to a point that makes inhalation difficult for the patient.

As best shown in FIGS. 28 and 29, The pressurized gas nozzle 726 and nozzle cover are shaped such that movement of the nozzle cover 732 from an actuated position (FIG. 28) to a non-actuated position (FIG. 29) both moves the fluid outlet away from the low pressure zone created by the gas flow diverted by the fixed diverter 746 and quickly cuts off the fluid pathways 734. When the nebulizer is actuated, a supply of fluid is steadily drawn up the fluid pathways 734 and provided at the fluid outlet. In order to avoid rapidly forcing excess fluid remaining in the fluid pathway out of the fluid outlet when the nozzle cover is moved to the non-actuated position, the upper portion of the nozzle 726 is fabricated with a cut-off region that cooperates with the inner diameter of the upper end of the nozzle cover to quickly cut off the fluid pathways. The cut-off region may simply be an area 797 of increased diameter close to the tip of the nozzle that fits tightly against the nozzle cover. In this manner, only a limited amount of fluid remaining in the extreme upper section 798 of the fluid pathway 734 will be displaced.

Referring to FIG. 25, the relief piston 762 preferably consists of a flexible material 790 covering the openings 763 in the lid 711. The flexible material, which may be constructed from plastic, metal or other suitably flexible substance, is captured by a central post 792 integral with the lid and preloaded against a ridge 791 so that the relief piston will not open until a desired negative pressure is reached in the chamber of the nebulizer. Another embodiment of the relief piston 793 is illustrated in FIG. 26. In this embodiment, the relief piston 793 consists of a rigid valve 794 biased against the ridge 791 to cover the openings 763 in the lid 711. A biasing member 795, such as a metal leaf spring, pre-loads the rigid valve against the ridge 791. The rigid valve may be made of any rigid material, such as polypropylene. In operation, the rigid valve 794 slides up and down the post 796 extending from the lid 711. The biasing member 795 may be mounted on the post 796 using any of a number of techniques, including friction fit, heat staking and so on The embodiments of FIGS. 21-27 include some additional features for improving the flexibility and performance of the nebulizer. For example, referring to FIGS. 21 and 23, an embodiment of the reservoir 780 is illustrated where the interior of the sloped lower wall 730 defining the reservoir is lined with a plurality of vertical ribs 788. The ribs 788 may cover all, or a portion, of the inside of the lower wall 730 and preferably extend up to the top of the lower portion 716 of the housing. Occasionally, fluid that is to be nebulized will collect on the wall of the reservoir due to condensation effects and from larger nebulized particles impacting against the wall. This fluid will typically only drop back into the main pool of fluid in the reservoir when the particles become large enough so that the force of gravity can overcome the surface tension keeping them stuck to the walls. The ribs 788 define corresponding vertical grooves or channels 789 that can assist in allowing droplets to more rapidly return to the pool of fluid in the reservoir The sharp angle of the ribs preferably keep droplets from forming on the tips of the ribs so that there is less area for droplets to attach. The ribs 788 may help to direct the droplets into the channels 789 where the droplets may accumulate more quickly and fall back into the reservoir. Although the ribs disclosed in FIGS. 21-27 are shown as triangular in cross-section, other rib shapes such as semicircles, rectangles and other shapes, may be fabricated. Additionally, a variety of differently shaped ribs and channels may be combined.

Another aspect of the nebulizer shown in FIGS. 21-27 is the continuous nebulization selection lever 782. The lever 782 is rotatably mounted in a chamber 786 on the middle portion 714 of the housing. The lever includes a threaded portion 784 positioned to engage the upper lip 766 of the actuator piston 738 The lever 782 may be manually rotated to allow the nebulizer 710 to operate in a breath actuated mode or a continuous nebulization mode. In the breath-actuated mode, the threaded portion 784 of the lever 782 does not contact the upper lip 766 of the actuator piston 738 so that the actuator piston may freely operate in the manner previously described As shown in FIG. 27, when the lever is rotated to put the nebulizer in continuous nebulization mode, the threaded portion 784 holds the actuator piston by the upper lip 766 so that the actuator piston, and attached nozzle cover, are in the actuated position and continuously nebulize any fluid in the reservoir. Although a horizontally rotatable lever 782 is shown, other two position switches or mechanisms, may be used.

Another embodiment of a breath-actuated nebulizer 800 is illustrated in FIGS. 30-32. The nebulizer 800 of FIGS. 30-32 is substantially similar to the embodiment illustrated in FIGS. 21-24 with the exception of the gas nozzle 826 and nozzle cover 832 configuration. The nozzle cover 832 defines an exit port 836 aligned with the pressurized gas orifice 828 in the nozzle 826. The diameter of the exit port 836 is preferably smaller than the outer diameter of the top portion 827 of the nozzle 826. In the actuated position, as shown in FIG. 31, the actuator piston 838 (FIG. 30) lifts the nozzle cover 832 so that a gap 829 is maintained between the top portion 827 of the nozzle 826 and the underside 830 of the top of the nozzle cover 832. The pressurized gas that is continuously fed through the nozzle 826 can then draw fluid from the reservoir 880 through the fluid pathway 834. The gas and fluid interact in the gap 829 and form an aerosol before exiting the exit port 836 in the nozzle cover 832. The aerosol then exits through the exit port where it is entrained against a diverter 846 to diverter out larger particles in the aerosol flow that was created in the gap 829 underneath the nozzle cover. Preferably, the diverter 846 is fixedly positioned in the nebulizer 800. In alternative embodiments, the diverter may be attached to the nozzle cover so as to maintain a constant distance between the exit port and the diverter, or the diverter may be movable independently of the movable nozzle cover.

During exhalation, or at rest, the actuator piston 838 lowers the nozzle cover 832 until the underside 830 of the top of the nozzle cover 832 rests against the top portion 827 of the nozzle 826. Although pressurized gas may still flow freely, the fluid pathway 834 is blocked off and fluid cannot be drawn from the reservoir 880. Thus, the gas nozzle 826 and nozzle cover 832 in FIGS. 30-32 are arranged in an internal mixing configuration such that the pressurized gas flow interacts with the fluid from the fluid pathway, or pathways, prior to leaving the exit port 836 in the nozzle cover 832. In contrast, the embodiment of FIGS. 21-24 illustrates an external mixing arrangement where the gas and fluid only interact outside of the nozzle and nozzle cover configuration and utilize a diverter to enhance the interaction between the gas and the fluid to promote formation of an aerosol. Additionally, or alternatively, the fluid inlet 835 at the base of the nozzle cover may be used to control fluid flow to the top of the nozzle in coordination with a patient's breathing. As discussed in the previous embodiments, the nozzle cover 832 movement can be used to press the fluid inlet 835 against the reservoir 880 wall or to move a collar that blocks off the fluid inlet 835.

The invention may be embodied in other forms than those specifically disclosed herein without departing from its spirit or essential characteristics. The described embodiments are to be considered in all respects only as illustrative and not restrictive, and the scope of the invention is intended to be commensurate with the appended claims.

We claim:

1. A nebulizer comprising:

a housing having an ambient air inlet and a chamber for holding an aerosol;

an air outlet communicating with the chamber for permitting the aerosol to be withdrawn from the chamber;

a gas inlet adjacent a moveable fluid orifice, the gas inlet in communication with the chamber, wherein the moveable fluid orifice comprises an opening defined by an outer diameter of the gas inlet and an inner diameter of an end of a gas inlet cover;

a diverter positioned in the chamber relative to the gas inlet; and, a nebulization activation member accessible outside the housing, the nebulization activation member operably connected with the moveable fluid orifice and configured to maintain the nebulizer in a first operational mode at a first setting, and in a second operational mode at a second setting, wherein at the first setting the nebulization activation member is positioned to maintain the fluid orifice in a nebulizing position and the first operational mode comprises continuous nebulization.

2. The nebulizer of claim 1, wherein at least one portion of the moveable fluid orifice is adjustable in response to a patient's breathing in the second operational mode.

3. The nebulizer of claim 2, further comprising an actuator piston connected with a gas inlet cover defining a portion of the fluid orifice and positioned in the housing, the actuator piston responsive to an initial period of inhalation through the air outlet to adjust the moveable fluid orifice to the nebulizing position when the nebulization activation member is at the second setting.

4. The nebulizer of claim 3, further comprising a relief piston located in the housing, the relief piston movable separately from the actuator piston and responsive to additional negative pressure in the chamber, after an initial period of inhalation, to allow increased air flow from the air inlet into the chamber, whereby an effort necessary for a patient inhaling through the air outlet is reduced.

5. The nebulizer of claim 1, wherein the diverter is in a fixed position relative to the gas inlet.

6. The nebulizer of claim 1, wherein the gas inlet comprises a cone-shaped nozzle and the gas inlet cover comprises a cone-shaped sleeve coaxially positioned around the cone-shaped nozzle.

7. The nebulizer of claim 1, wherein the fluid orifice is in communication with a fluid reservoir positioned inside the nebulizer.

8. A nebulizer for providing an aerosol to a patient, the nebulizer comprising:

a housing having an air inlet and a chamber for holding the aerosol;

an air outlet communicating with the chamber for permitting the aerosol to be withdrawn from the chamber;

a gas inlet located in the chamber;

a fluid orifice located in the chamber adjacent the gas inlet, the fluid orifice in communication with a fluid pathway from a fluid reservoir, wherein the fluid orifice comprises an opening defined by an outer diameter of the gas inlet and an inner diameter of an end of a gas inlet cover;

a nebulization activation member accessible outside the housing, the nebulization activation member operably connected with the fluid pathway and configured to maintain the nebulizer in a first operational mode at a first setting, and in a second operational mode at a second setting, wherein in the first setting the nebulization activation member is positioned to maintain the fluid pathway in a nebulizing position and the first operational mode comprises continuous nebulization, wherein a flow of fluid from the fluid reservoir to the fluid orifice is uninterrupted; and an actuator piston movably positioned adjacent the air inlet and connected with at least a portion of the gas inlet cover, wherein the actuator piston and the at least a portion of the gas inlet cover are movable in response to inhalation at the air outlet, in the second operational mode.

9. The apparatus of claim 8, wherein the fluid pathway comprises at least one channel defined by a recessed longitudinal groove in at least one of the outer diameter of the gas inlet and the inner diameter of the gas inlet cover.

10. The apparatus of claim 8, wherein the gas inlet comprises a nozzle and the gas inlet cover comprises a nozzle cover coaxially positioned around the nozzle, wherein at least a portion of the nozzle cover is movable with respect to the nozzle.

11. A nebulizer comprising:

a housing having an ambient air inlet and a chamber for holding an aerosol;

an air outlet communicating with the chamber for permitting the aerosol to be withdrawn from the chamber;

a gas inlet adjacent a fluid orifice, the gas inlet in communication with the chamber;

a diverter positioned in the chamber relative to the gas inlet;

a nebulization activation member accessible outside the housing, the nebulization activation member operably connected with the chamber to control forming or disrupting a fluid pathway between a fluid reservoir and a fluid orifice and configured to maintain the nebulizer in a first operational mode at a first setting, and in a second operational mode at a second setting, wherein at the first setting the nebulization activation member is positioned to maintain the fluid pathway as a continuous fluid pathway and the first operational mode comprises continuous nebulization; and wherein at least one portion of the fluid orifice is adjustable in response to a patient's breathing in the second operational mode.

12. The nebulizer of claim 11, further comprising an actuator piston connected with a gas inlet cover defining a portion of the fluid orifice and positioned in the housing, the actuator piston responsive to an initial period of inhalation through the air outlet to adjust the fluid orifice to a nebulizing position when the nebulization activation member is at the second setting.

13. The nebulizer of claim 12, further comprising a relief piston located in the housing, the relief piston movable separately from the actuator piston and responsive to additional negative pressure in the chamber, after an initial period of inhalation, to allow increased air flow from the air inlet into the chamber, whereby an effort necessary for a patient inhaling through the air outlet is reduced.

14. The nebulizer of claim 11, wherein the diverter is in a fixed position relative to the gas inlet.

15. The nebulizer of claim 11, wherein the fluid orifice comprises an opening defined by an outer diameter of the gas inlet and an inner diameter of an end of a gas inlet cover.

16. The nebulizer of claim 15, wherein the gas inlet comprises a cone-shaped nozzle and the gas inlet cover comprises a cone-shaped sleeve coaxially positioned around the cone-shaped nozzle.

\* \* \* \* \*

UNITED STATES PATENT AND TRADEMARK OFFICE
CERTIFICATE OF CORRECTION

| | | |
|---|---|---|
| PATENT NO. | : 7,905,228 B2 | |
| APPLICATION NO. | : 11/542619 | |
| DATED | : March 15, 2011 | |
| INVENTOR(S) | : Blacker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 920 days.

Signed and Sealed this
Ninth Day of August, 2011

David J. Kappos
*Director of the United States Patent and Trademark Office*